United States Patent [19]
Levy et al.

[11] Patent Number: 5,202,310
[45] Date of Patent: Apr. 13, 1993

[54] CYCLOSPORINE METABOLITES

[76] Inventors: Gary A. Levy, 15 Gainsville Avenue, Unionville, Ontario, Canada, L3R 1W7; Pui Y. Wong, 5 Radway Avenue, Etobicoke, Ontario, Canada, M9C L17

[21] Appl. No.: 534,090

[22] Filed: Jun. 6, 1990

[51] Int. Cl.$^5$ .............. A61K 37/00; A61K 37/02; C07K 5/00; C07K 7/00
[52] U.S. Cl. .................... 514/11; 530/317; 530/321
[58] Field of Search ................ 530/317, 321; 514/11

[56] References Cited

U.S. PATENT DOCUMENTS 4,639,434  1/1987  Wenger et al. ............ 514/11
4,703,033  2/1988  Seebach .
4,771,122  9/1988  Seebach ................ 530/317

OTHER PUBLICATIONS

Wang et al., Chemical Abstracts, vol. 111 No. 9, 1989, Abst. #70239u.
Kim et al., Biological Abstracts, vol. 90 No. 7, 1990, Abstr. #79269, Oct. 1, 1990.
Cole et al. Transplant. Proc. 21:943, 1989.
Cheung et al. Transplant. Proc. 20, Suppl. 2:602, 1988.
Cheung et al. Transplant. Proc. 20, Suppl. 2:633, 1988.
Bowers et al. Transplant. Proc. 20, Suppl. 2:597, 1988.
Ryffel et al. Transplant. Proc. 20, Suppl. 2:575, 1988.
Abecassis et al. Can. J. Surg. 31:145, 1988.
Schlitt et al. Transplant. Proc. 19:4248, 1987.
Freed et al. Transplantation 43:123, 1987.
Dindzans et al. Transplant Proc. 19:3490, 1987.
Kahan Transplantation 40:457, 1985.
Maurer Transplant. Proc. 17, Suppl. 1:19, 1985.
Maurer et al. Drug Metab. Dispos. 12:120, 1984.
Kahan et al. Transplant. Proc. 15:446, 1983.
Powell-Jackson et al. Transplantation 36:505, 1983.

Primary Examiner—Merrell C. Cashion, Jr.
Assistant Examiner—A. M. Davenport
Attorney, Agent, or Firm—Bereskin & Parr

[57] ABSTRACT

A cyclosporine metabolite having a molecular weight determined by mass spectrometry of about 1205 and having the following properties: (a) being immunologically distinct from cyclosporine metabolites OL-1, OL-17 and OL-8; (b) being more polar than OL-1 or OL-17 and less polar than OL-8 when eluated from a gradient high performance liquid chromatography; (c) being extractable from bile of test animals which have been administered cyclosporine A; and (d) being substantially free of other cyclosporine metabolites and cyclosporine A, and a physiologically acceptable salt or stereoisomer thereof.

10 Claims, 31 Drawing Sheets

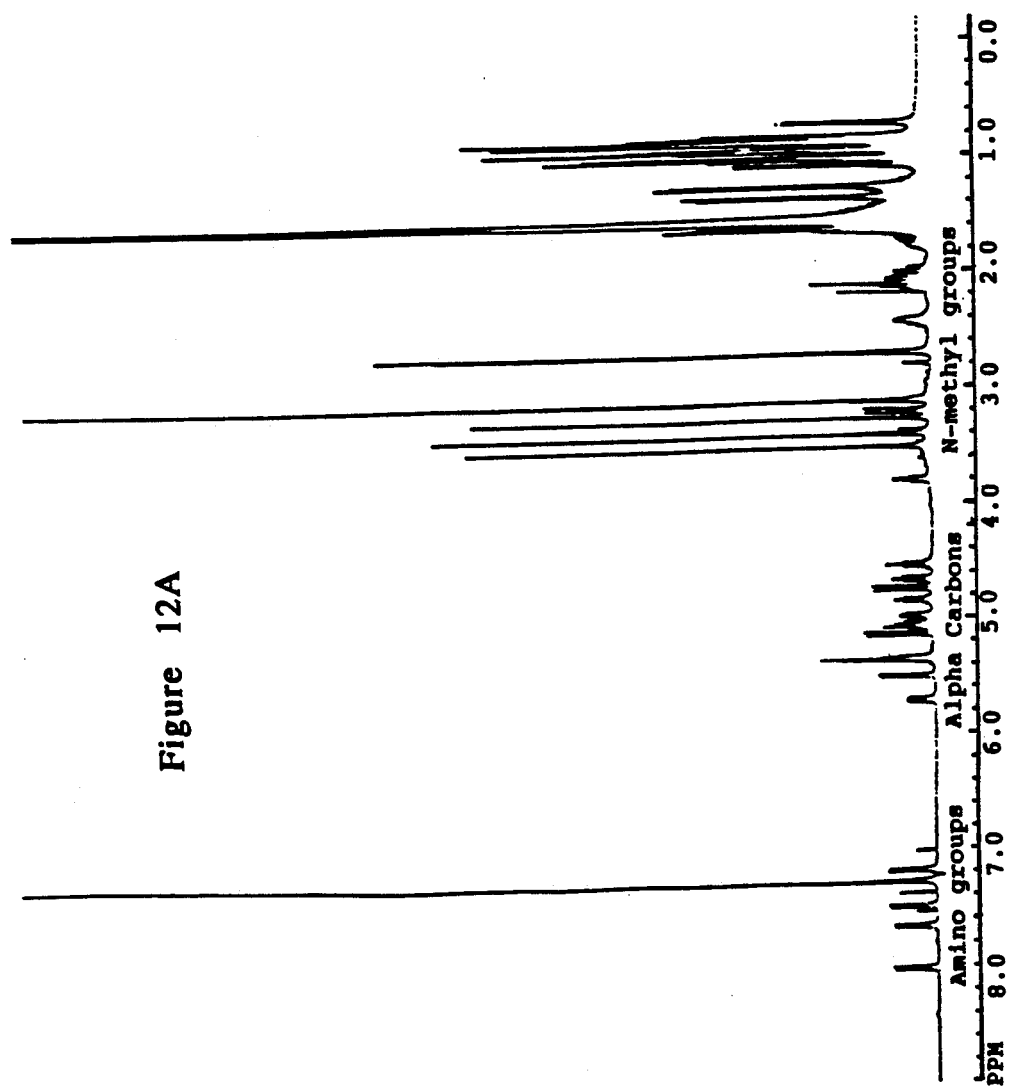

CYCLOSPORINE METABOLITES

FIELD OF THE INVENTION

The present invention relates to novel cyclosporine metabolites, their use as pharmaceuticals, and pharmaceutical compositions containing the novel cyclosporine metabolites. The invention also relates to a method of isolating the novel cyclosporine metabolites.

BACKGROUND OF THE INVENTION

Cyclosporin A (CsA) is a biologically active product of the fungus *Trichoderma polysporum* (Calne, R. Y., Immunol. Rev. 46: 113-124, 1979). It is a chemically neutral, extremely hydrophobic cyclic polypeptide composed of 11 amino acids (Petcher, T. J. et al, Helv. Chim. Acta 59:1480, 1976) and has been represented by the following formula A:

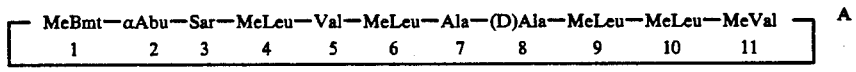

wherein -MeBmt- represents the N-methyl-(4R)-4-but-2E-en-1-yl-4-methyl-(L)-threonyl residue of the formula B:

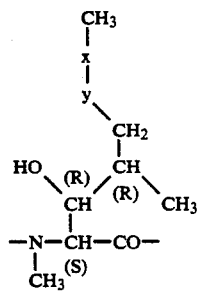

in which —x—y— is —CH=CH—(trans.) (U.S. Pat. No. 4,703,033 to Seebach, P.). The amino acid residues in formula A are referred to by conventional abbreviations, and the same numerical sequence and abbreviations are employed in the specification and claims.

CsA is a potent immunosuppressive agent that is widely used in organ transplantation (White, D. J. G. (ed): Cambridge, England, Elsevier Biomedical, September, 1981; and Cohen, D. J. et al, Ann. Int. Med. 101:667, 1984). The clinical use of CsA, however, is limited by significant CsA toxicity, especially nephrotoxicity, at the recommended therapeutic dosage (Shulman, H. et al, N. Engl. J. Med. 305:1392, 1981; Klintmalm, G. B. G. et al, Lancet, 1:470, 1981; and Kahan, B. D., Transplantation, 40:457, 1985).

CsA in vitro has been found to be extensively metabolized by hepatic cytochrome P-450 microsomal enzymes, and has been found predominantly in its metabolite forms (cyclosporine metabolites) (CM) (Maurer, G. et al, Drug Metab. Dispos. 12:120, 1984; Kahan B. D., Transplant. Proc. 15:446, 1983; and, Maurer, G., Transplant. Proc. 17:19, 1985). CM constitutes well over 70% of cyclosporins found in whole blood, and well over 90% of cyclosporins found in bile of allograft recipients (Cheung, F. Transplant. Proc. 20:602, 1988). The primary metabolites of hepatic CsA metabolism which have been detected are the monohydroxylated derivatives designated OL-17 (in the human), and OL-1 (in the rat), and OL-21 its N-methylated derivative (Venkataraman, R. et al, Transplant. Proc. 20:759, 1988). Other minor CM have been detected; however, their structural identity and purity have hitherto not been established (Cheung, F., Transplant. Proc. 20:602, 1988; and Bowers, L. D. et al, Transplant. Proc. 20:597, 1988).

The role of CM in immunosuppression and toxicity is not clearly documented. CM in vivo have been reported by many investigators to have varying degrees of immunosuppression as compared with the parent CsA. Mauer, G. (Transplant. Proc. 17:19, 1985) Schlitt, N. J. (Transplant. Proc. 19:4248, 1987) and Ryffel, B. (Transplant. Proc. 20:575, 1988) have reported fewer immuno- suppressive effects as compared with the parent CsA. Freed, B. M. (Transplantation 43:123, 1987) have reported comparable effects of OL-17, followed by OL-1 and OL-21, to CsA in the ability to inhibit lymphocyte proliferation in a mixed lymphocyte reaction and IL2 production. The present inventors have reported equal or superior immunosuppressive activity of some CM, as measured both by the ConA proliferative assay and mixed lymphocyte reaction (Dindzans V. and Wong, P. Y., Transplant. Proc. 19:3490, 1987; and Abecassis, M. et al, Can. J. Surg. 31:145, 1988).

Experiments in rats utilizing inducers of the cytochrome P-450 oxidase system have demonstrated that some CM were unlikely to be causative agents of nephrotoxicity (Powell-Jackson, P. R. et al, Transplantation 36:505, 1983, and Goldberg, H. J. Transplantation 47:731, 1989). Ryffel, B. et al (Transplant. Proc. 20:575,1988) have reported that OL-17 was not toxic in vivo in the rat. The present inventors have also shown that some CM are much less toxic to renal and mesangial cells in culture than parent CsA (Cole, et al, Transplant. Proc. 21:943, 1989).

The studies described above are of limited utility in defining the role of individual CM in immunosuppression and toxicity since the composition and purity of many of the CM fractions used in the studies are unknown. As indicated in Bowers, L. D. et al (Transparent. Proc. 20:597, 1988) at page 597, it is imperative that the compounds be isolated and their structural identity and purity be established in order to clearly document the role of CM in the activity and toxicity of CsA.

SUMMARY OF THE INVENTION

The present inventors have isolated and identified a novel cyclosporine metabolite (hereinafter referred to as cyclosporine metabolite H(CM-H) from the bile of liver transplant patients who have been administered CsA. The novel CM-H has been found to be distinct from known CM. In particular, CM-H has been found to be chromatographically eluatable at a short retention time from a gradient high performance liquid chromatography (HPLC). It showed more polarity than monohydroxylated CM such as OL-1 (9-OH-CsA) or OL-17 (1-OH-CsA). CM-H demonstrated less polarity than CM OL-8 (1,9 di-OH-CsA). The novel metabolite has also been shown to be immunologically distinct from prior art CM. For example, CM-H was shown to be unreactive with a monoclonal antibody which has no specificity towards amino acid residue 6 and weakly recognizes amino acid residue 1 CsA, and with an anti- CsA monoclonal antibody which recognizes amino acid residues 1 and 6 of CsA. The novel metabolite, however, was shown to be reactive with polyclonal anti-cyclosporine antibody. The molecular weight of CM-H was determined to be 1205 by fast atom bombardment mass spectrometry (FABMS). FABMS and nuclear magnetic resonance (NMR) data further indicated that CM-H has the structure of CsA shown in formula A, but in which the amino acid residue at the 9-position is hydroxylated and the amino acid residue at the 10-position is demethylated.

The present invention, therefore, relates to a cyclosporine metabolite having a molecular weight determined by mass spectrometry of about 1205 and having the following properties:

a) being immunologically distinct from cyclosporine metabolites OL-1, OL-17 and OL-8;

b) being more polar than OL-1 or OL-17 and less polar than OL-8 when eluated from a gradient high performance liquid chromatography (HPLC);

c) being extractable from bile of test animals which have been administered cyclosporine A; and d) being substantially free from other cyclosporine metabolites and cyclosporine A, and a physiologically acceptable salt or stereoisomer thereof.

Preferred cyclosporine metabolites in accordance with the invention are those substantially having the structure of cyclosporine A and having a hydroxylated α-N-methylated α-amino acid residue at the 9-position and an α-N-demethylated α-amino acid at the 10-position. Especially preferred cyclosporine metabolites in accordance with the present invention are those having the following formula I:

wherein X is a hydroxylated α-N-methylated α-amino acid, and Y is an α-N-demethylated α-amino acid residue. In a most preferred embodiment of the invention the cyclosporine metabolites are those having the following formula II:

or carrier. The invention further relates to a method of inducing immunosuppression in a patient comprising administering to said patient an effective amount of a cyclosporine metabolite of the invention. The invention still further relates to the use of a cyclosporine metabolite of the invention in the prophylaxis and treatment of diseases and conditions requiring a reduction of the immune response.

DESCRIPTION OF THE DRAWINGS

The invention will be better understood with reference to the drawings in which:

FIG. 3A shows the resulting chromatogram where a C8 column with isocratic elution are employed in the HPLC.

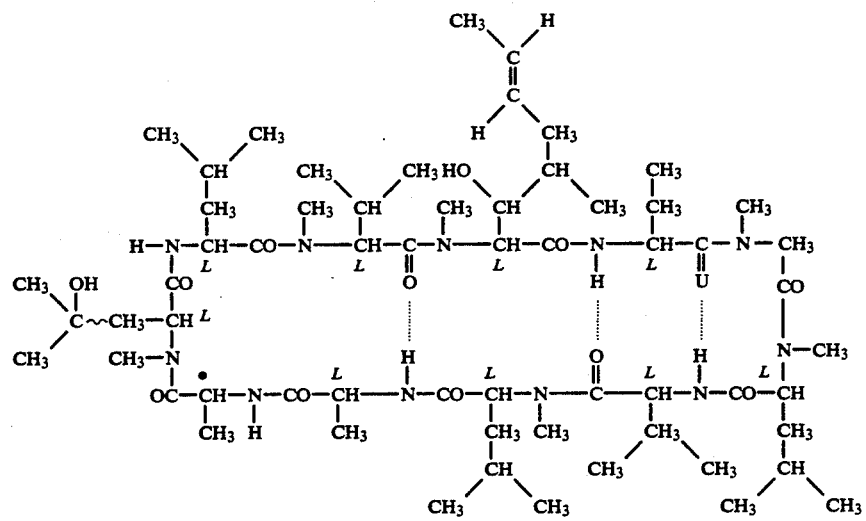

Figure 7:
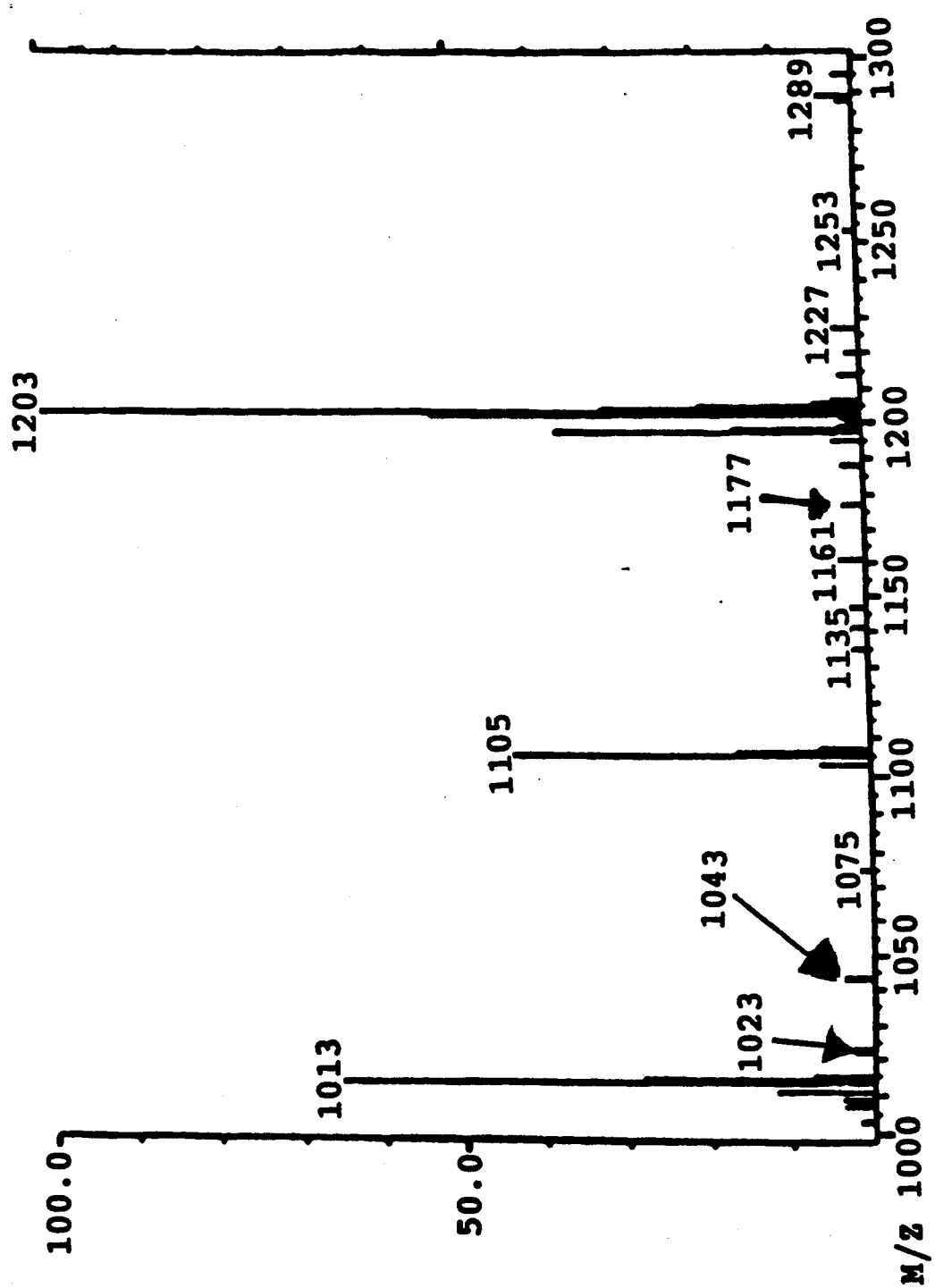
Figure 7:
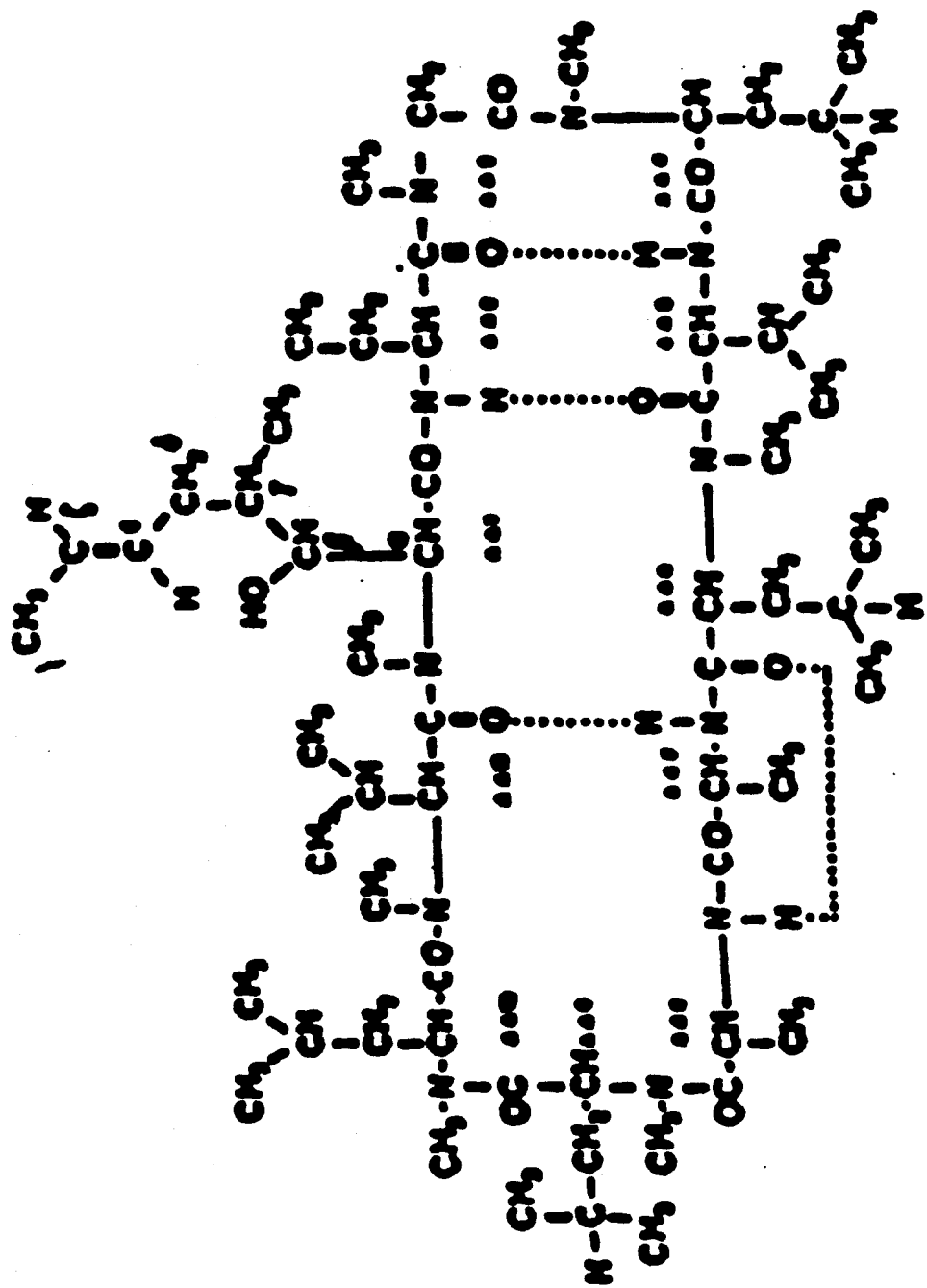

The invention also relates to a pharmaceutical composition comprising a novel cyclosporine metabolite of the invention and a pharmaceutically acceptable diluent FIG. 7 is a partial positive ion fast atomic bombardment mass spectrum of cyclosporine-A parent.

Figure 8:
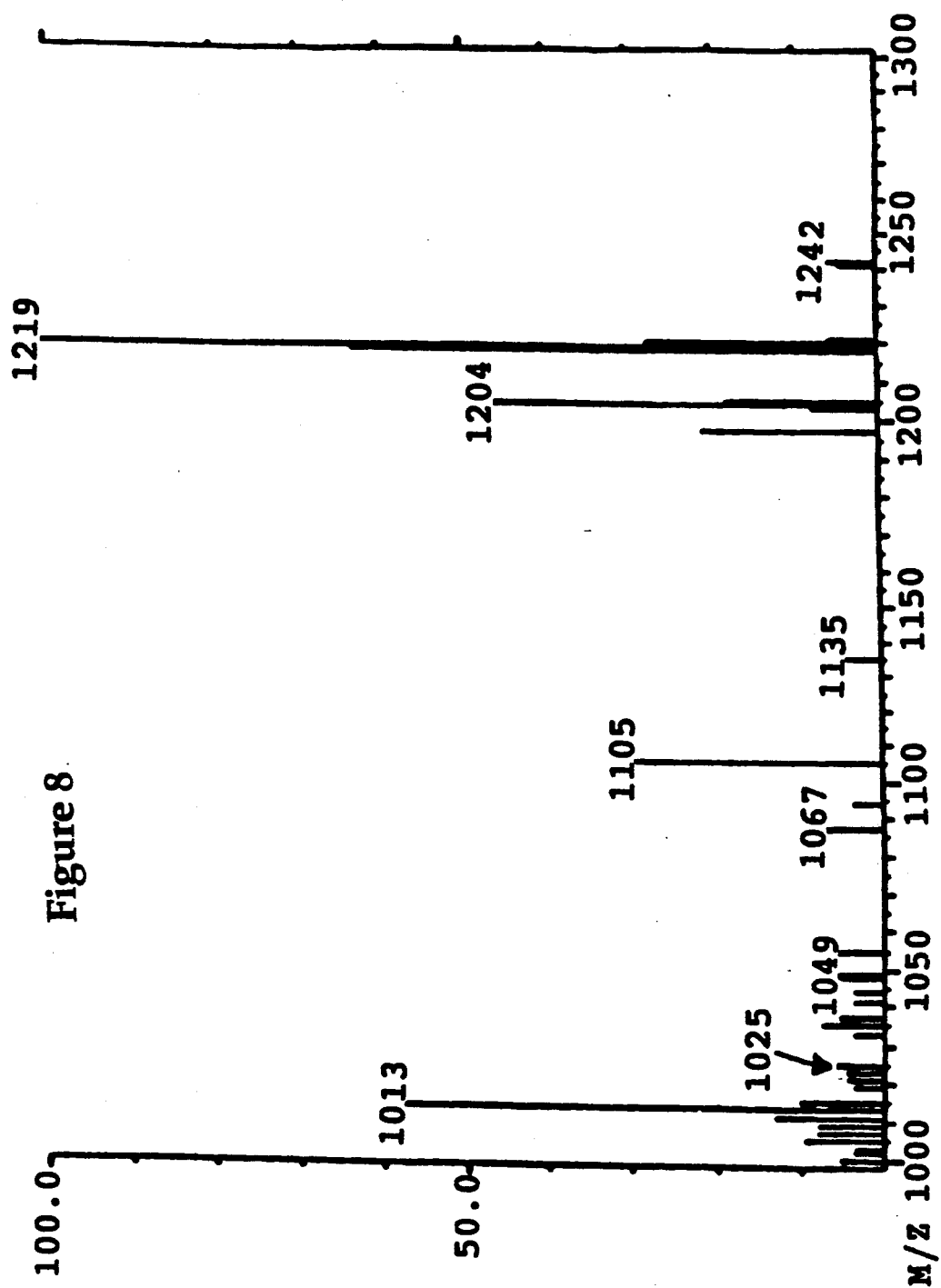
Figure 8:
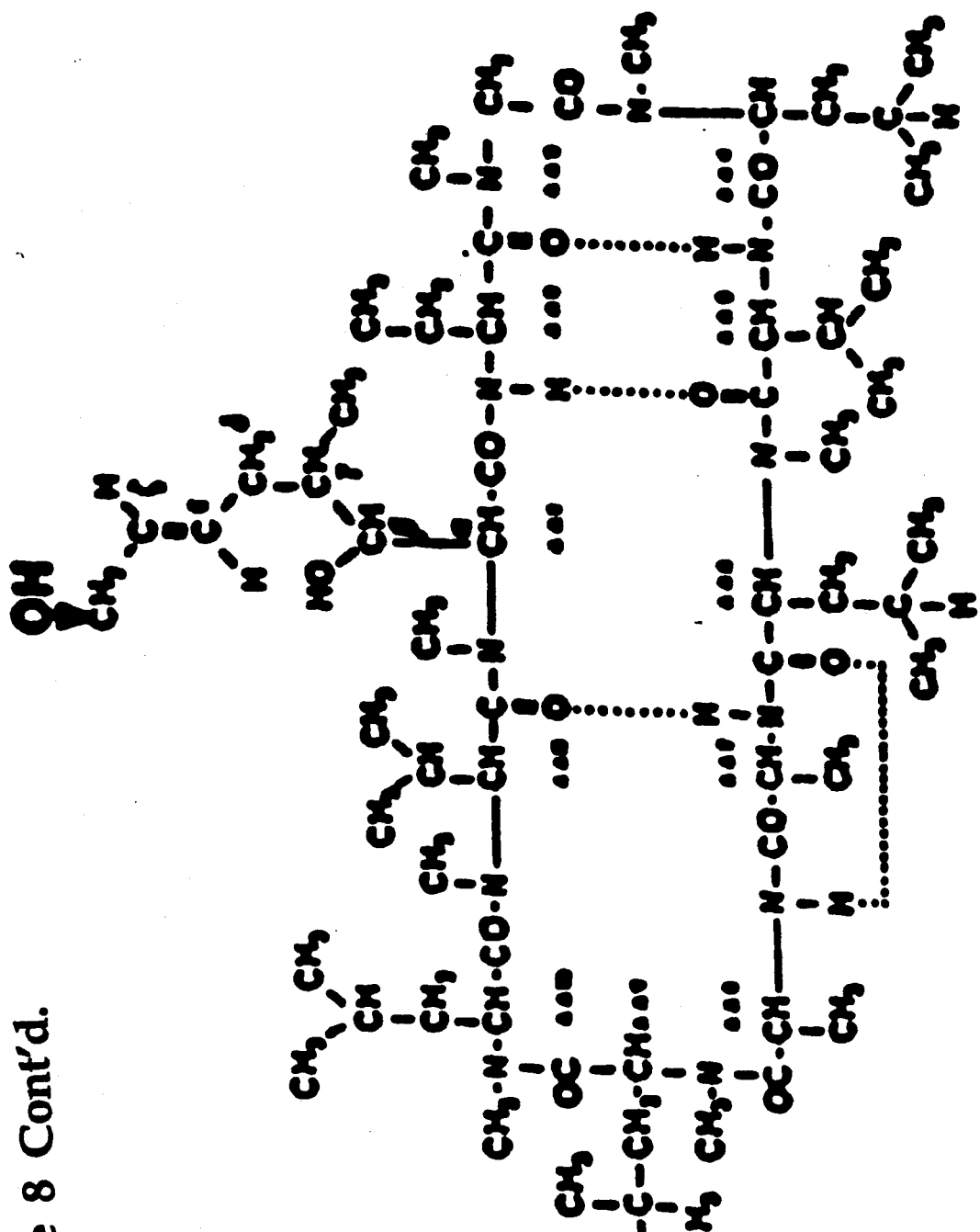

FIG. 8 is a partial positive ion fast atomic bombardment mass spectrum of cyclosporine metabolite OL-17 (1-hydroxy cyclosporine A).

Figure 9:
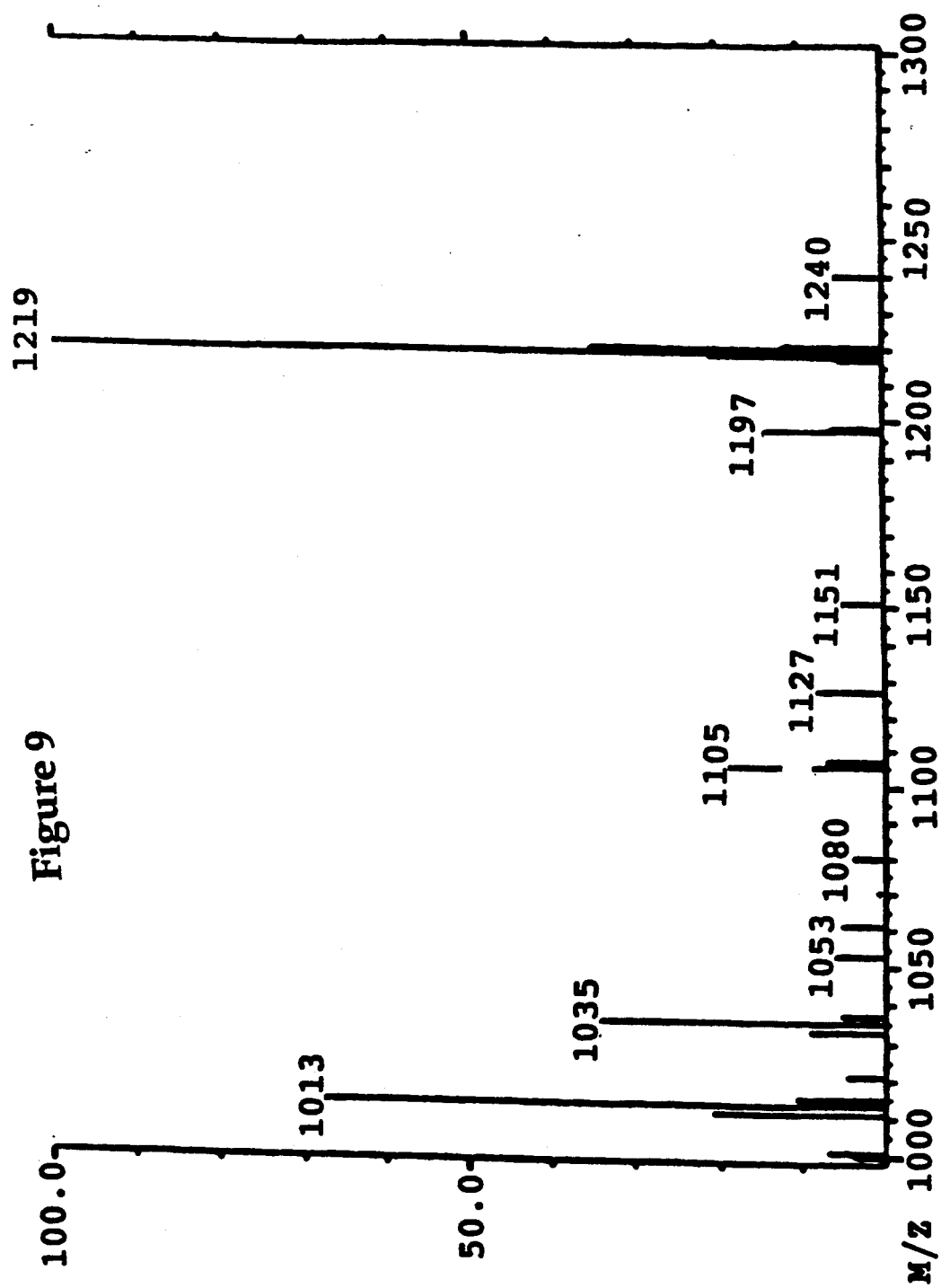
Figure 9:
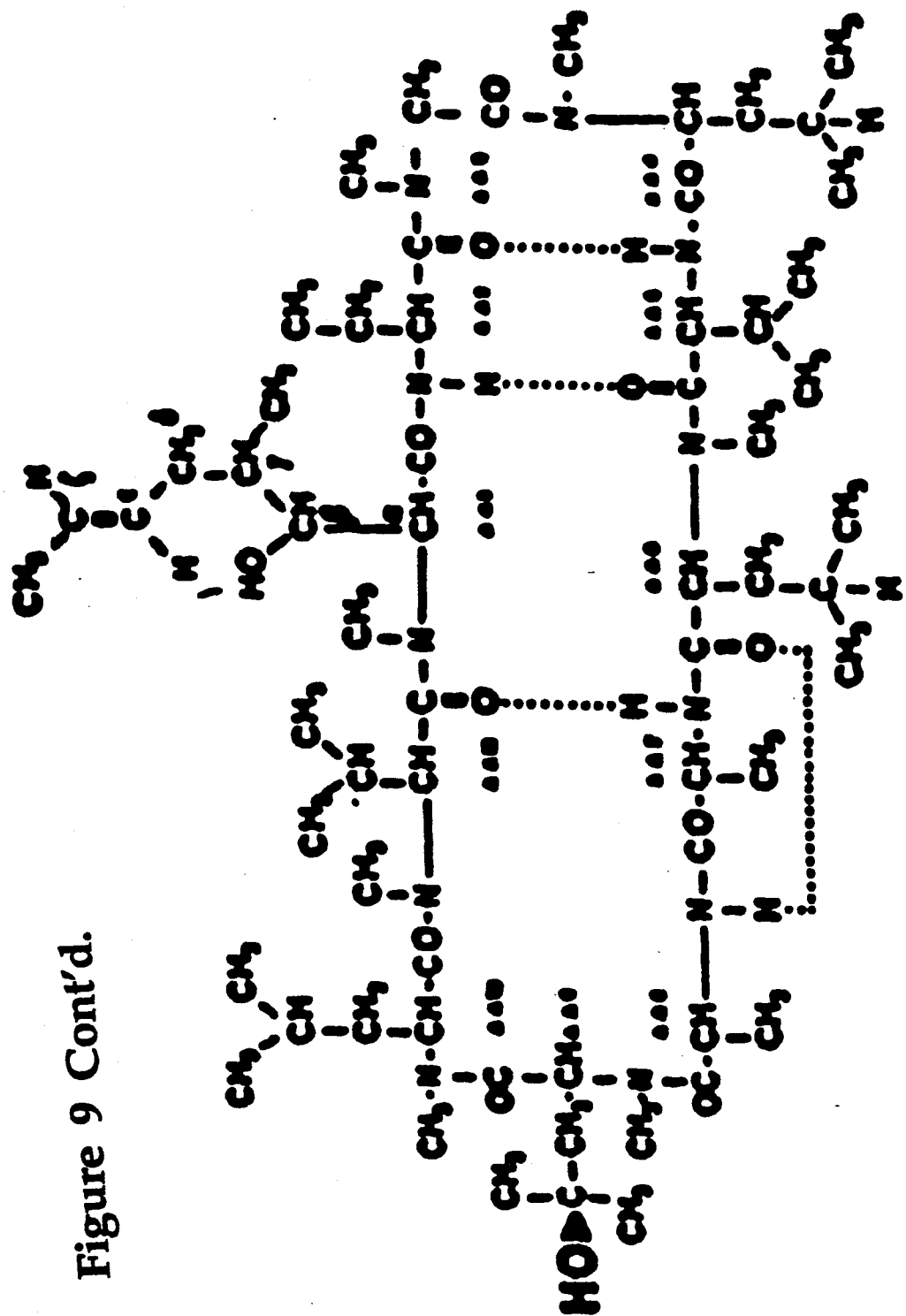

FIG. 9 is a partial positive ion fast atomic bombardment mass spectrum of the cyclosporine metabolite OL-1 (9-hydroxy cyclosporine A).

Figure 10:
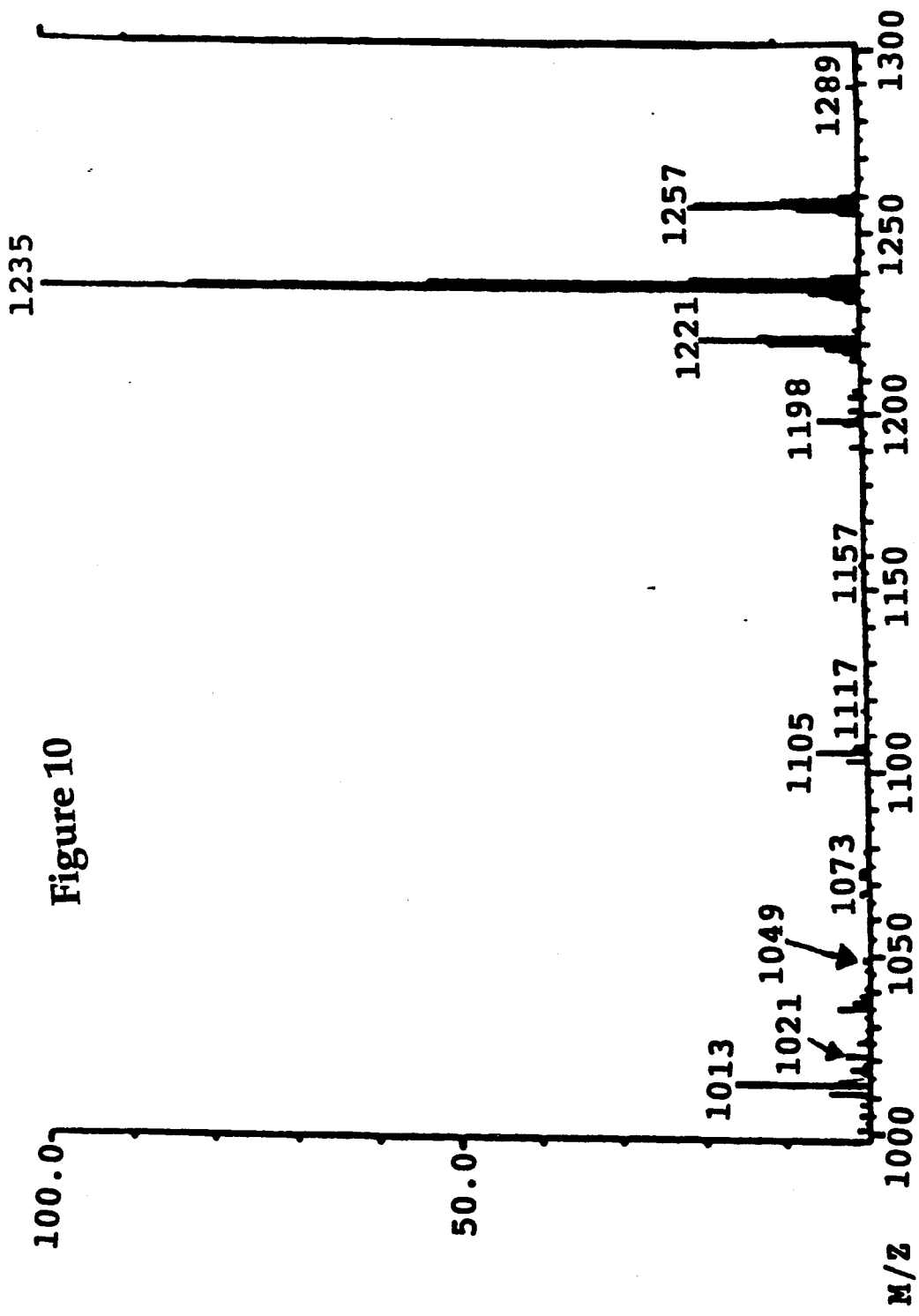
Figure 10:
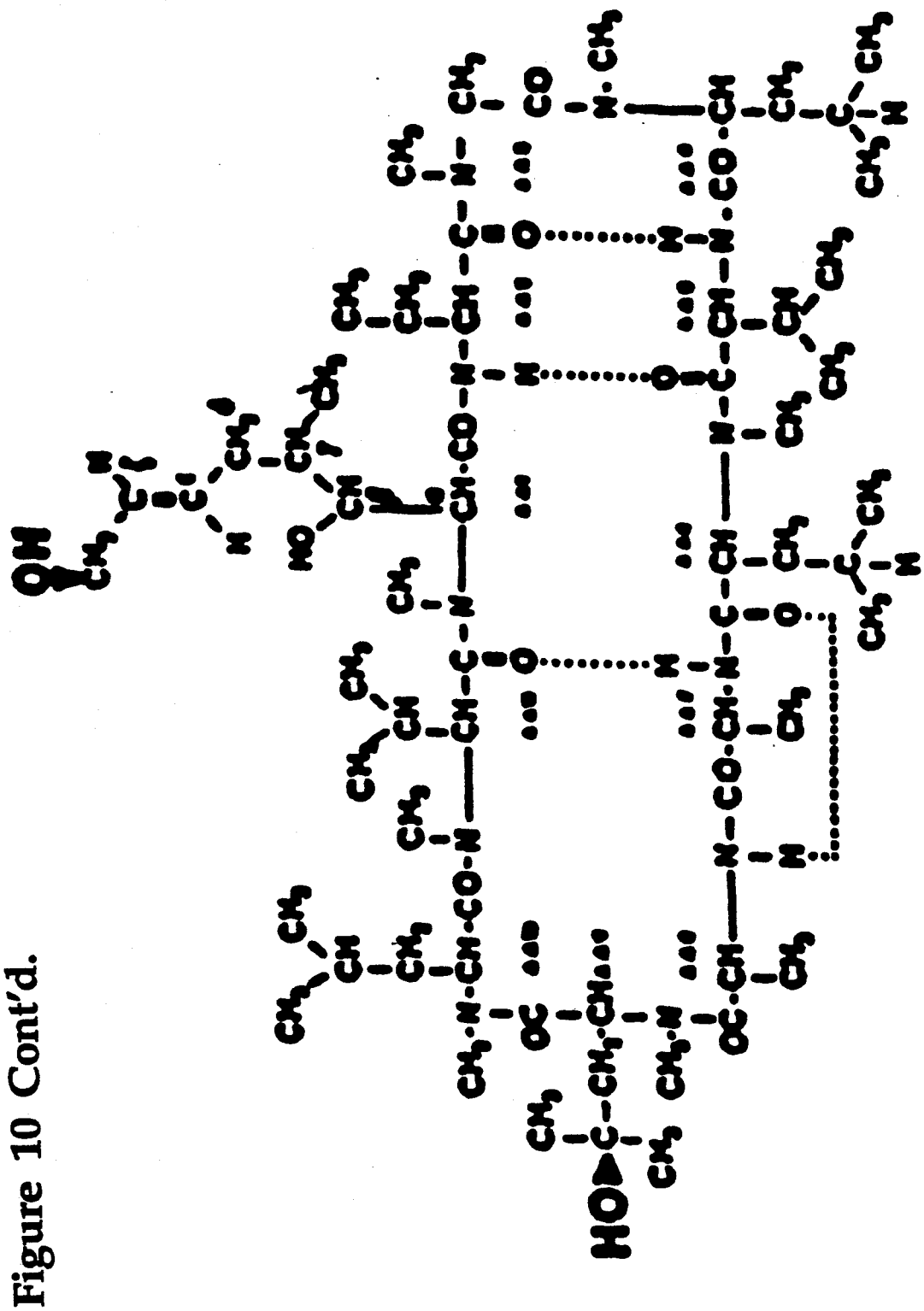

FIG. 10 is a partial positive ion fast atomic bombardment mass spectrum of the cyclosporine metabolite OL-8 (1,9 dihydroxy cyclosporine A).

Figure 11:
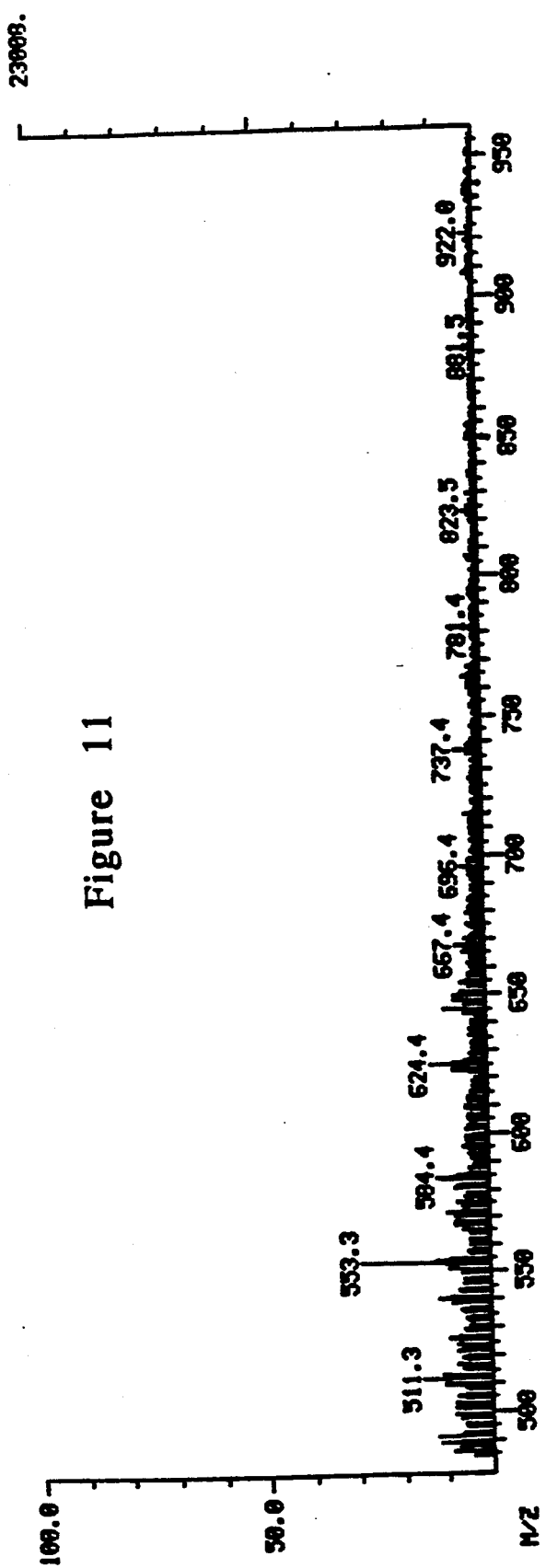
Figure 11:
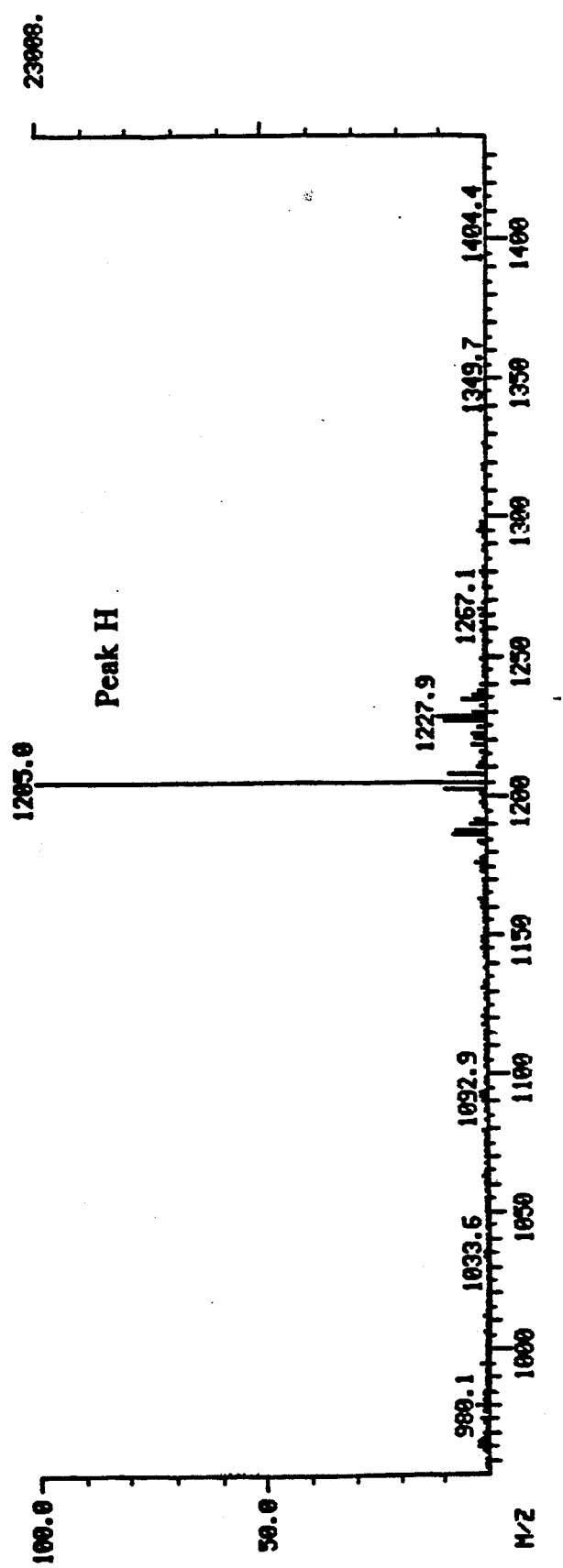

FIG. 11 is a positive ion fast atomic bombardment mass spectrum of a cyclosporine metabolite of the invention.

FIG. 12A and B is a comparative NMR spectrum of CsA parent (A) and the cyclosporine metabolite of the invention (B).

Figure 13:
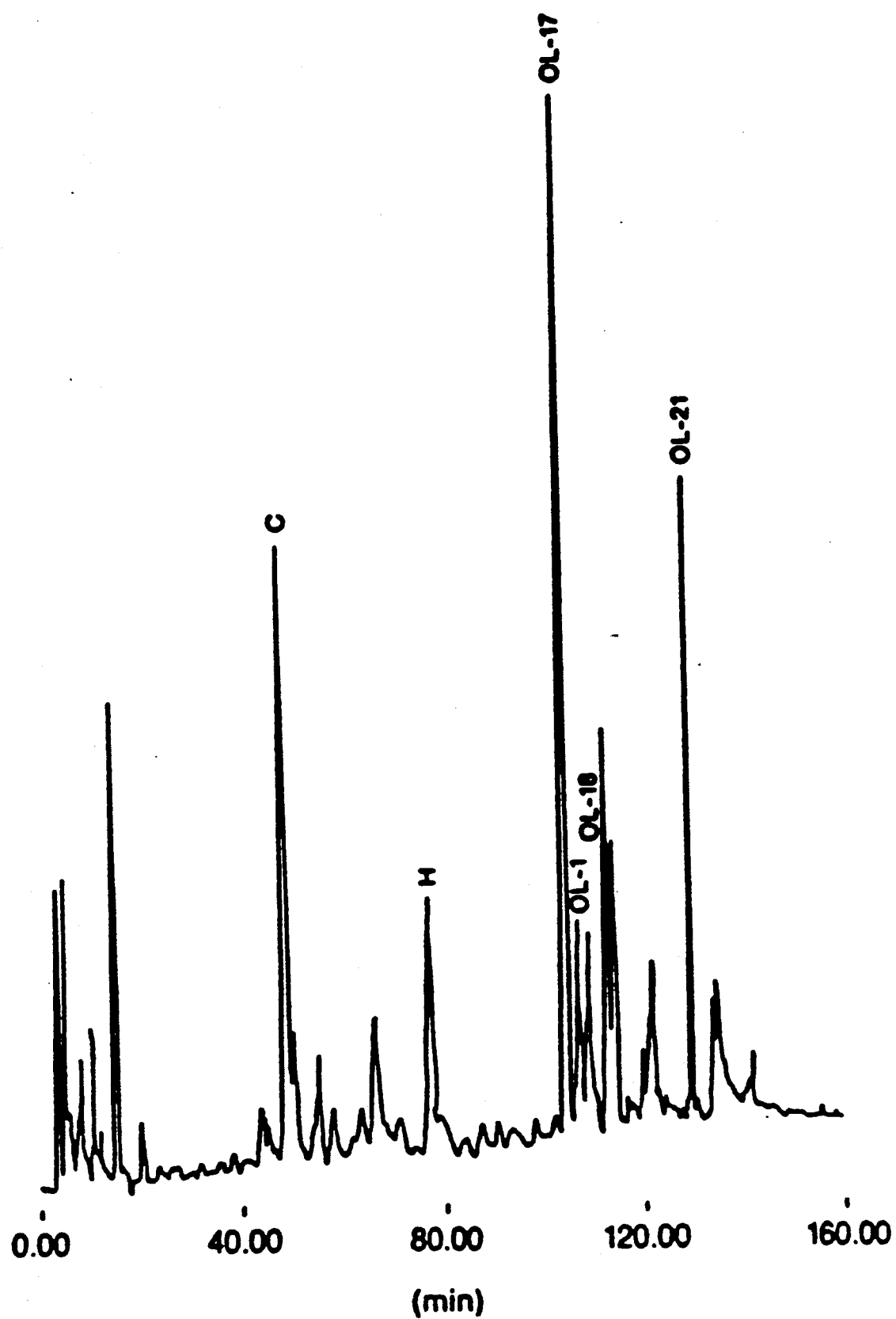

FIG. 13 is an elution profile of extracted CM from the bile of liver transplant patients using UV spectroscopy.

Figure 14A:
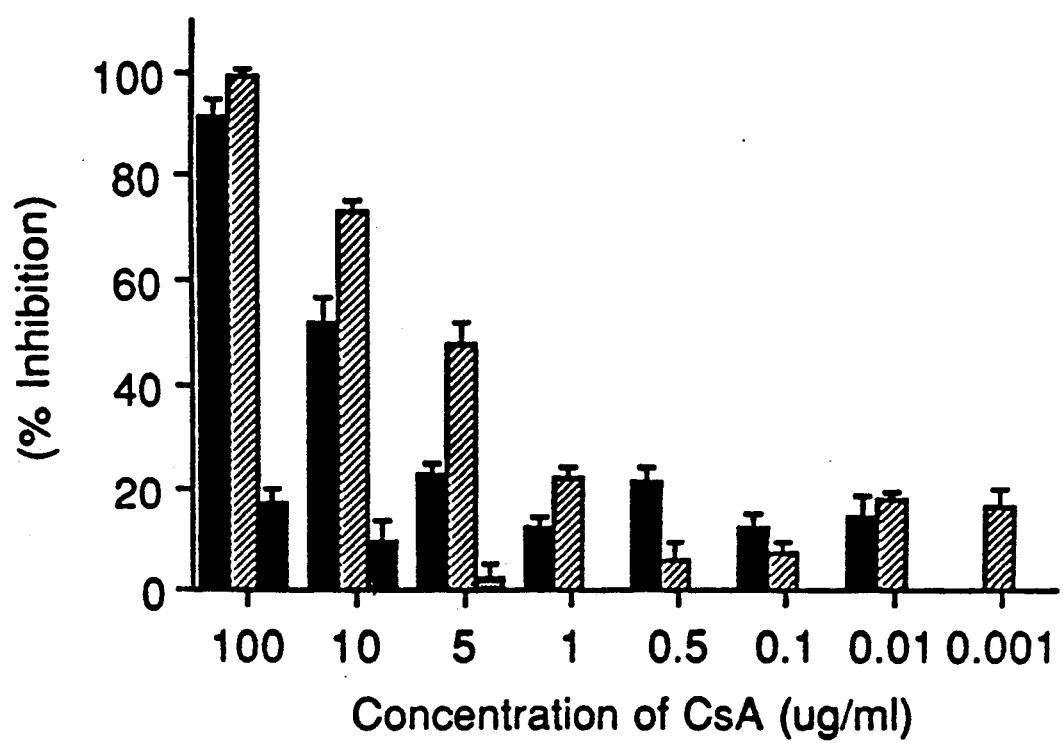

FIG. 14A, B and C are bar graphs showing the effects on DNA (FIG. 14A), RNA (FIG. 14B) and protein (FIG. 14C) synthesis of renal epithelial, renal mesangial cell lines and murine lung cell line L2.

Figure 15A:
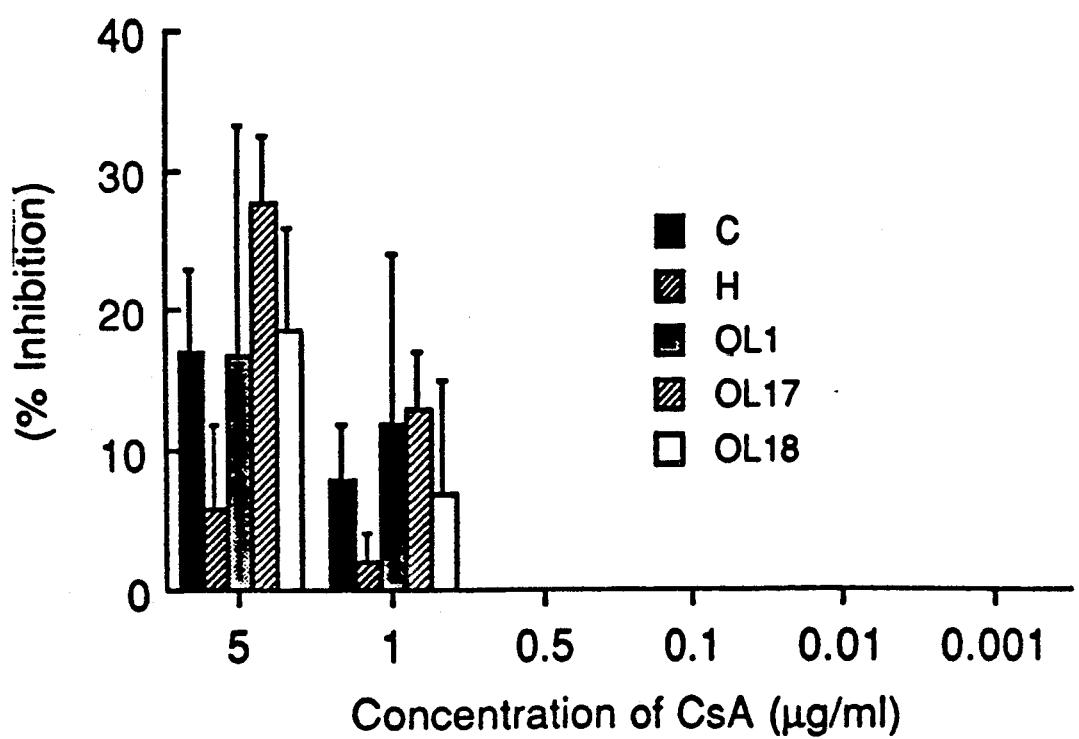

FIG. 15A, B, and C are bar graphs showing the effects of the individual metabolites OL-1, OL-17, OL-18, OL-8 and the metabolite of the invention on DNA(A), RNA(B) and protein (C) synthesis in renal mesangial cells.

DETAILED DESCRIPTION OF THE INVENTION

As hereinbefore described the invention relates to a cyclosporine metabolite having a molecular weight determined by mass spectrometry of about 1205 and having the following properties:

a) being immunologically distinct from cyclosporine metabolites OL-1, OL-17 and OL-8;

b) being more polar than OL-1 or OL-17 and less polar than OL-8 when eluated from a gradient high performance liquid chromatography (HPLC);

c) being extractable from bile of test animals which have been administered cyclosporine A; and d) being substantially free from other cyclosporine metabolites and cyclosporine A, and a physiologically acceptable salt or stereoisomer thereof.

Preferred cyclosporine metabolites in accordance with the invention are those substantially having the structure of cyclosporine A and having a hydroxylated α-N-methylated α-amino acid residue at the 9-position and an α-N-demethylated α-amino acid at the 10-position. Especially preferred cyclosporine metabolites in accordance with the present invention are those having the following formula I:

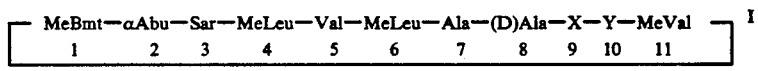

wherein X is a hydroxylated α-N-methylated α-amino acid, and Y is an α-N-demethylated α-amino acid residue. In a most preferred embodiment of the invention the cyclosporine metabolites are those of the formula II:

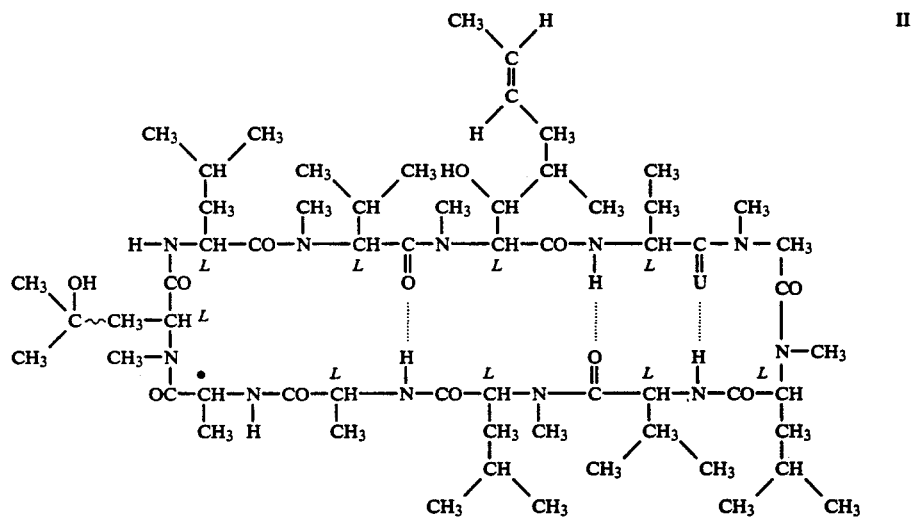

The cyclosporine metabolites according to the invention may exist in stereoisomeric forms which behave as image and mirror image (enantiomers) or which do not behave as image and mirror image (diastereomers). The invention relates to both the antipodes and the racemic forms and also mixtures of diastereomers.

The cyclosporine metabolites according to the invention may be present in the form of their salts. In general, these are salts with inorganic or organic acids. However, the physiologically acceptable salts of the metabolites according to the invention with inorganic and organic acids are preferred.

Figure 1:
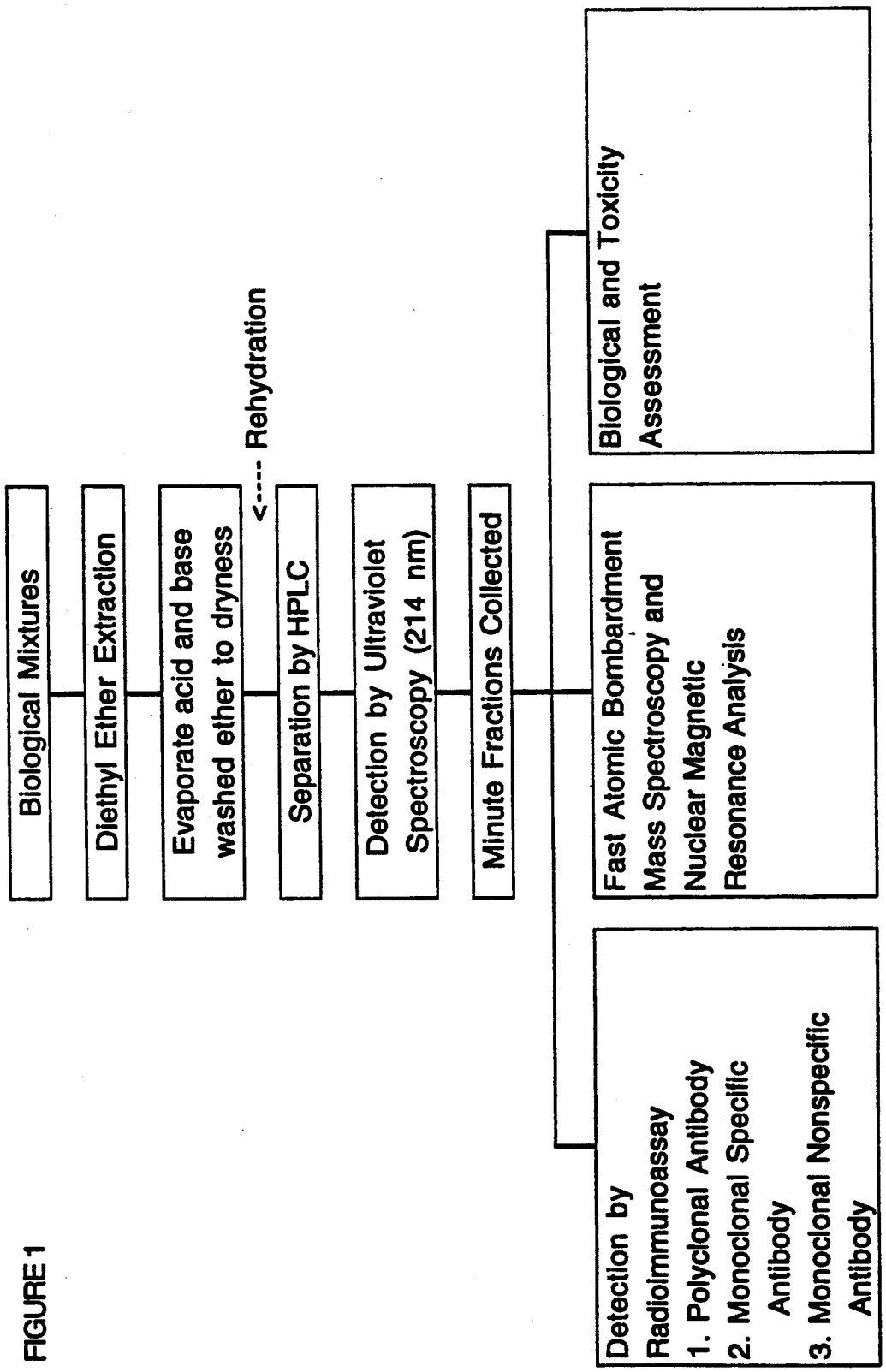
FIG. 1 is a schematic illustration of a method of isolating the cyclosporine metabolite of the invention from a biological sample.

The cyclosporine metabolites of the invention may be obtained from bile of an animal which has been administered CsA, for example, using the procedure generally described below and schematically set out in FIG. 1.

Bile samples from liver transplant recipients are extracted with diethyl ether, the ether extracts are combined and evaporated, and the residue is reconstituted with acetonitrile:methanol:water. The novel cyclosporine metabolites of the invention are resolved using high-pressure liquid chromatography (HPLC). The novel cyclosporine metabolites of the invention display a short retention time off the HPLC and they demonstrate stronger polarity than monohydroxylated CM such as OL-1 (9-OH-CsA) or OL-17 (1-OH-CsA) and less polarity than CM OL-8 (1,9 di-OH-CsA). The resolved novel cyclosporine metabolites of the invention may be detected by assaying the eluated fractions using a solid phase radioimmunoassay. In particular, the metabolites may be detected using polyclonal anti-cyclosporine antibody, monoclonal antibody which has no specificity towards amino acid residue 6 and weakly recognizes amino acid residue 1 of CsA, and monoclonal antibody which recognizes amino acid residues 1 and 6 of CsA. The metabolites of the invention are reactive with the polyclonal antibody and unreactive with the monoclonal antibodies. The molecular composition of the resolved cyclosporine metabolites of the invention may be confirmed by subjecting eluted fractions containing the metabolites to fast atomic bombardment mass spectroscopy (FABS).

The new cyclosporine metabolites of the invention have valuable pharmacological properties. In particular, the new cyclosporine metabolites of the invention have immunosuppressive activity. They are also characterized by reduction of undesirable side-effects, for example, reduction of toxicity especially nephrotoxicity, as compared to hitherto known cyclosporine metabolites such as CM OL-17, OL-1, OL-18, and OL-8 and CsA as may be demonstrated in DNA, RNA and protein inhibition assays in renal and mesangial cells. They may be used as immunosuppressive agents for the prophylaxis and treatment of disease and conditions requiring a reduction of the immune response. They are thus especially useful in suppressing the proliferation of lymphocytes and immunocytes, for example, in the treatment of autoimmune diseases or in preventing the rejection of transplants including liver, kidney, skin and bone-marrow transplants.

The new cyclosporine metabolites of the invention are indicated for use in the treatment of autoimmune diseases for which treatment with CsA has been proposed or used including aplastic anaemia, pure red cell anaemia, idiopathic thrombocytopaenia, systemic lupus erythematodes, polychondritis, scleroderma, Wegener's granulamatosis, dermatomyositis, chronic active hepatitis, myasthenia gravis, psoriasis, Steven-Johnson syndrome, idiopathic sprue, Crohn's disease, Graves opthalmopathy, sarcoidosis, multiple sclerosis, primary biliary cirrhosis, primary juvenile diabetes, uveitis posterior, interstitial lung fibrosis and psoriatic arthritis.

The cyclosporins are known to inhibit T-cell proliferation and thus are indicated as therapeutic agents either alone or in conjunction with other therapeutic agents in the prophylaxis and treatment of disease caused by leucotropic retroviruses, for example HTLV-I or III. It is thus anticipated that the new cyclosporine metabolites of the invention will be useful in the prophylaxis and treatment of these diseases. The new cyclosporine metabolites of the invention may also be suitable for the treatment of inflammatory conditions and parasitic diseases.

The new cyclosporine metabolites of the invention may be converted using customary methods into pharmaceutical compositions, such as tablets, capsules, dragees, pills, granules, aerosols, syrups, emulsions, suspensions, and solutions using inert, non-toxic, pharmaceutically acceptable excipients or solvents. The new cyclosporine metabolites are present in the pharmaceutical composition in amounts which suffice to achieve the indicated dosage range. The concentration of the metabolites may be similar to the concentration generally used for cyclosporins, in particular up to about 1 to 50 mg/ml may be used.

The pharmaceutical compositions are prepared, for example by combining the new cyclosporine metabolites of the invention with solvents and/or excipients, using emulsifiers and/or dispersing agents, if appropriate, and, for example where water is employed as a dilutent, organic solvents may be used as auxiliary solvents if appropriate.

Examples of excipients or solvents which may be used in the pharmaceutical compositions are water, non-toxic organic solvents, such as paraffins (for example petroleum fractions), vegetable oils (for example groundnut oil/sesame oil), alcohols (for example ethyl alcohol and glycerine), glycols (for example propylene glycol and polyethylene glycol), solid excipients such as, for example, natural rock powders (for example kaolins, aluminas, talc and chalk), synthetic rock powders (for example highly disperse silica and silicales) and sugars (for example sucrose, lactose and glucose), emulsifiers (for example polyoxyethylene-fatty acid esters, polyoxyethylene-fatty alcohol ethers, alkylsulphonates and arylsulphonates), dispersing agents (for example lignin, sulphite waste liquors, methyl cellulose, starch and polyvinylpyrrolidone) and lubricants (for example magnesium stearate, talc, stearic acid and sodium laurylsulphate).

Administration of the pharmaceutical composition is effected in the customary manner, preferably orally, parenterally, or intravenously. In the case of oral use, capsules and tablets may also contain, in addition to the excipients mentioned above, additives such as sodium citrate, calcium carbonate and dicalcium phosphate, together with various further substances such as starch, gelatine and the like. Lubricants, for example magnesium stearate, sodium laurylsulphate and talc may be used conjointly for tablet-making. In the case of aqueous suspensions and/or elixirs which are intended for oral use, the new cyclosporine metabolites of the invention may be mixed with various flavour-improving agents or dyestuffs in addition to the above-mentioned auxiliaries.

In the case of intravenous and parenteral administration, solutions, suspensions or emulsions of the new cyclosporine metabolites of the invention can be employed, using suitable liquid vehicles.

In general, a dosage range is envisaged for administration in human medicine of from about 0.1 to 20, preferably from about 0.1 to 10, most preferably 1 to 5 mg/kg of body weight daily may be employed. In the case of intravenous administration, the preferred dosage is about 0.1 to 5 mg/kg of body weight daily, most preferably 1 mg/kg of body weight daily and in the case of oral administration the dosage is about 1 to 5 mg/kg of body weight daily, most preferably 3 to 5 mg/kg of body weight daily.

It will also be appreciated that it may be necessary to deviate from the amounts mentioned and in particular to do so as a function of the body weight of the animal to be treated, the particular disease to be treated, the nature of the administration route and the therapy desired. In addition, the type of animal and its individual behaviour towards the medicine or the nature of its formulation and the time or interval at which it is administered may also indicate use of amounts different from those mentioned. Thus it may suffice, in some cases, to manage with less than the above-mentioned minimum amounts whilst in other cases the upper limit mentioned must be exceeded. Where major amounts are administered, it may be advisable to divide these into several administrations over the course of the day.

EXAMPLE 1

Isolation of CM a) Extraction of CM and CsA parent:

Bile was collected from orthotopic liver transplanted patients who had a T-tube inserted for the purpose of establishing bile flow. Urine and whole blood were also collected from the patients. All samples were stored at $-70°$ C. until use.

Two major extractants were employed to extract CM from the bile samples. These two extractants were diethyl ether (BDH Tor. Can.) and ethyl acetate (Fisher. Miss. Cann.). Diethyl ether was the primary extractant employed to extract the biological specimens. In analytical HPLC, 1 to 20 mls of biological fluids were extracted. For preparative HPLC, 30 to 50 mls of biological fluids were generally employed.

The detailed steps of the extraction procedure are set out below.

The biological specimens were first acidified to between pH 4 and 5 with 180 mM HCl prior to the extraction step. Acidified biological specimens were then extracted with diethyl ether (BOH Toronto, Canada) twice at a ratio of three parts of extractant to one part of biological specimen. The extractant was then collected, pooled and back washed twice with 95 mM NaOH. This washing step removed many unwanted endogenous substances. The acid-and base-washed extractant was again collected, pooled and evaporated to dryness at 37° C. under vacuum. The dried specimens were covered with parafilm and stored at 4° C.

b) High Pressure Liquid Chromatography- (HPLC) Separation System

A Waters gradient HPLC system (Waters Ass. Milford, Mass.) was used to separate the CM and parent CsA in the specimens. The hardware consisted of two dual piston HPLC pumps (model 501 and 510), two U6K injectors (one preparative-2 ml capacity and one analytical-500 $\mu$l), an automated gradient controller, an ultra-violet 214 nm absorbance detector (model 441), a data module (740 series), a TCM temperature regulator and a LKB 2112 redirac fraction collector (LKB Bromma. Sweden).

Separation was achieved through a C18 $\mu$bondapak 10 micron-analytical column, a C8 ultrasphere 5 micron-analytical column and a C8 Supelcosil 5 $\mu$m- semi-preparative column. Both analytical and preparative C8 columns were linked in tandem to provide more partitioning material to resolve the CM.

To elute the CM and CsA parent off the columns, two different strategies were employed. One strategy employed an isocratic form of elution. The mobile phase used for isocratic elution was composed of 50% Acetonitrile, 20% Methanol and 30% deionized water. The second strategy used a linear gradient form of elution. In this linear gradient elution system, the mobile phase was made up of two parts. One part was composed of 90% deionized water and 10% Methanol. The other part was composed of 90% Acetonitrile and 10% Methanol.

Four different systems were employed to resolve the CM from each other as well as from the CsA parent. In all four systems, the dried specimens obtained as described above in (a) were rehydrated in the isocratic mobile phase. The resulting mixture was centrifuged at 800 xg for three minutes. The sample supernatant was then injected into the resolving column using a Hamilton syringe. One of the following four systems was then employed:

i) Isocratic C18 single column elution:

In this system, the resolving C18 (7 mm $\times$ 18 cm) was heated to 50° C. Sample supernatant was injected (10-500 uL) onto the heated column at an isocratic mobile phase flow rate of 1.5 ml/min. Two, ten ml fractions of eluate were collected. The first 10 fraction contained a mixture of CM and the second 10 ml fraction contained the CsA parent.

ii) Isocratic C8 single column elution:

In this system, a 500 $\mu$L of sample supernatant was injected into a 70° C. heated C8 (4.6 mm $\times$ 25 cm) column. The isocratic mobile phase flow rate was set at 1 ml/min. Sixty, 0.75 ml fractions (approximately 20 drops per tube) of CsA and CM were collected.

iii) Isocratic two C8 columns in tandem elution:

In this system an additional C8 column was linked in tandem to the preexisting C8 column in system (ii) described above. Other operating parameters were identical to system (ii) described above except that one hundred and twenty, 1 ml fractions of CsA and CM were collected at one minute intervals instead of sixty fractions.

iv) Analytical and preparative gradient two C8 columns in tandem elution:

The sample mixture capacity that was injected onto the heated C8 columns (10 mm $\times$ 25 mm) for separation was increased to 2 ml.

In this elution system, CsA and its CM were collected analytically and preparatively. The columns were two C8 columns linked in tandem similar to the system described in (iii) above. Other analytical operating parameters were also similar with the exception that the eluting mobile phase is made up of two cocktails mixing linearly. The flow rate of the mobile phase was 1 ml/min for the analytical system and 4.7 ml/min for the preparative system. One hundred and sixty, one minute fractions of eluate were collected.

CM and CsA standards obtained from Sandoz Pharma (Basel, Switzerland) were also separated by gradient HPLC using the C8 columns in tandem as described above.

EXAMPLE 2

Detection of Resolved CM and CsA

Figure 2:
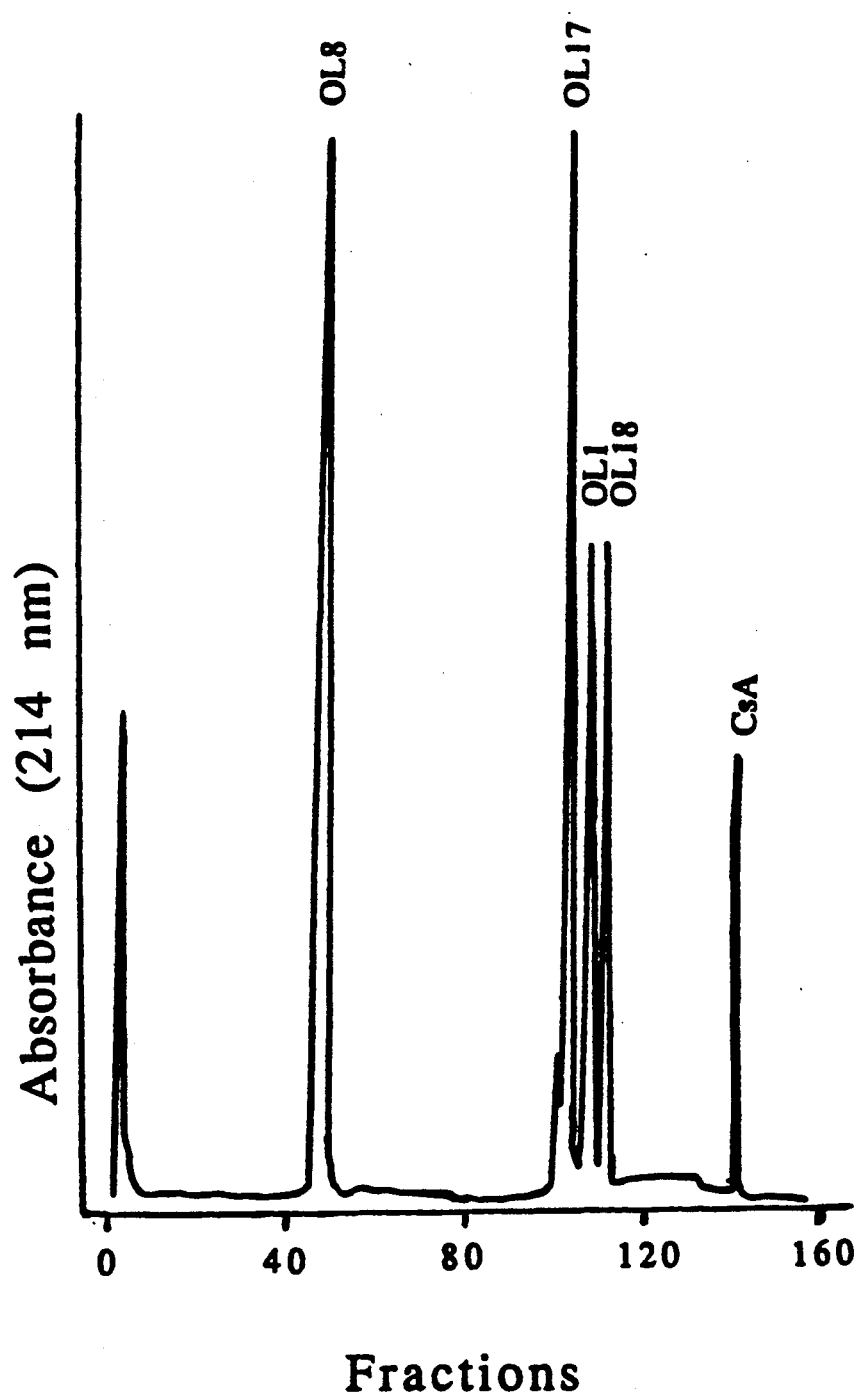
FIG. 2 is a graph showing CM and CsA standards which have been separated by gradient HPLC and detected by UV spectroscopy at 214 nm.

The concentration of the resolved CM and CsA was determined by ultraviolet spectroscopy (214 nm) as the fractions eluted off the reverse phase columns. The UV profile for the CM and CsA standards is shown in FIG. 2.

The amount of CM and CsA present in each fraction that was collected using the four HPLC elution strategies were assayed by RIA. The amount of CM and CsA detected was expressed as equivalent CsA units and replotted in the order in which the fractions were collected off the HPLC system.

The radioimmunoassays were in house biological assays or commercial kits (Incstar, Stillwater, Minn.) with detecting antibodies produced by Sandoz Pharma (Basel, Switzerland). In particular, a polyclonal anti-cyclosporin antibody was used. The extent of crossreactivity between CM and the polyclonal antibody ranged from 5% to 30%. Thus the amount of CM peak was expressed in CsA equivalents. A specific anti-CsA monoclonal antibody having strong recognition of amino acid residues 1 and 6 of CsA was used in the RIA to detect CsA. A monoclonal antibody which had no specificity towards amino acid residue 6 and weakly recognized amino acid residue 1 of CsA was used in the RIA to detect native CsA and CM.

The RIA procedure is detailed below. HPLC eluates, controls and standards were combined with Iodine-125 ($I^{125}$)-labelled cyclosporin derivative tracer, and polyclonal or monoclonal antibodies specific for CsA only, or CM and CsA, and were incubated for one hour. Iodo-cyclsporin tracer was made by labelling histamine conjugated cyclosporin C with Iodine$^{125}$ using the chloramine T method (Wong, P. Y. et al, Clin. Chem. 32:492, 1986). Following the one-hour incubation, a second antibody (donkey antimouse serum) and carrier (normal mouse serum) were added for approximately one hour to further interact with the bound immune complex. The tracer bound to the immune complex was separated from the unbound tracer by centrifuging at 2400 Xg for 15 minutes. The amount of radioactivity, as measured by a gamma counter, was inversely proportional to the concentration of cyclosporin found in the sample. The concentration of the sample was interpolated from a standard curve generated in the same assay. In the case of the tritium labelled tracer, the unbound tracer in the supernatant was decanted into 10 ml of Scintiverse I and its radioactivity was then measured in a beta counter.

Figure 3A:
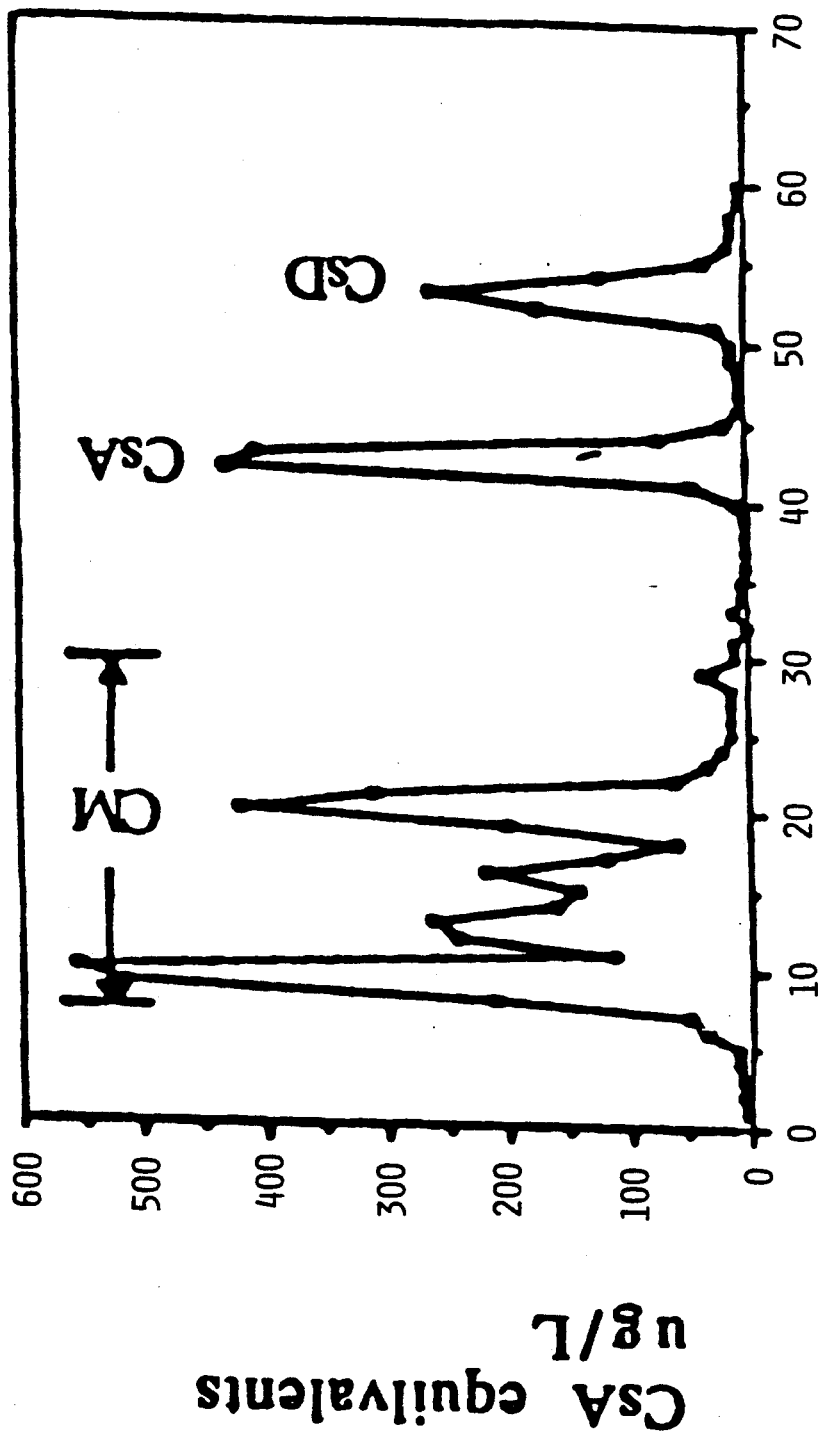
FIG. 3A, B and are HPLC/polyclonal antibody RIA chromatograms from a 24-hour urine sample in a CsA treated liver transplant patient.
Figure 3B:
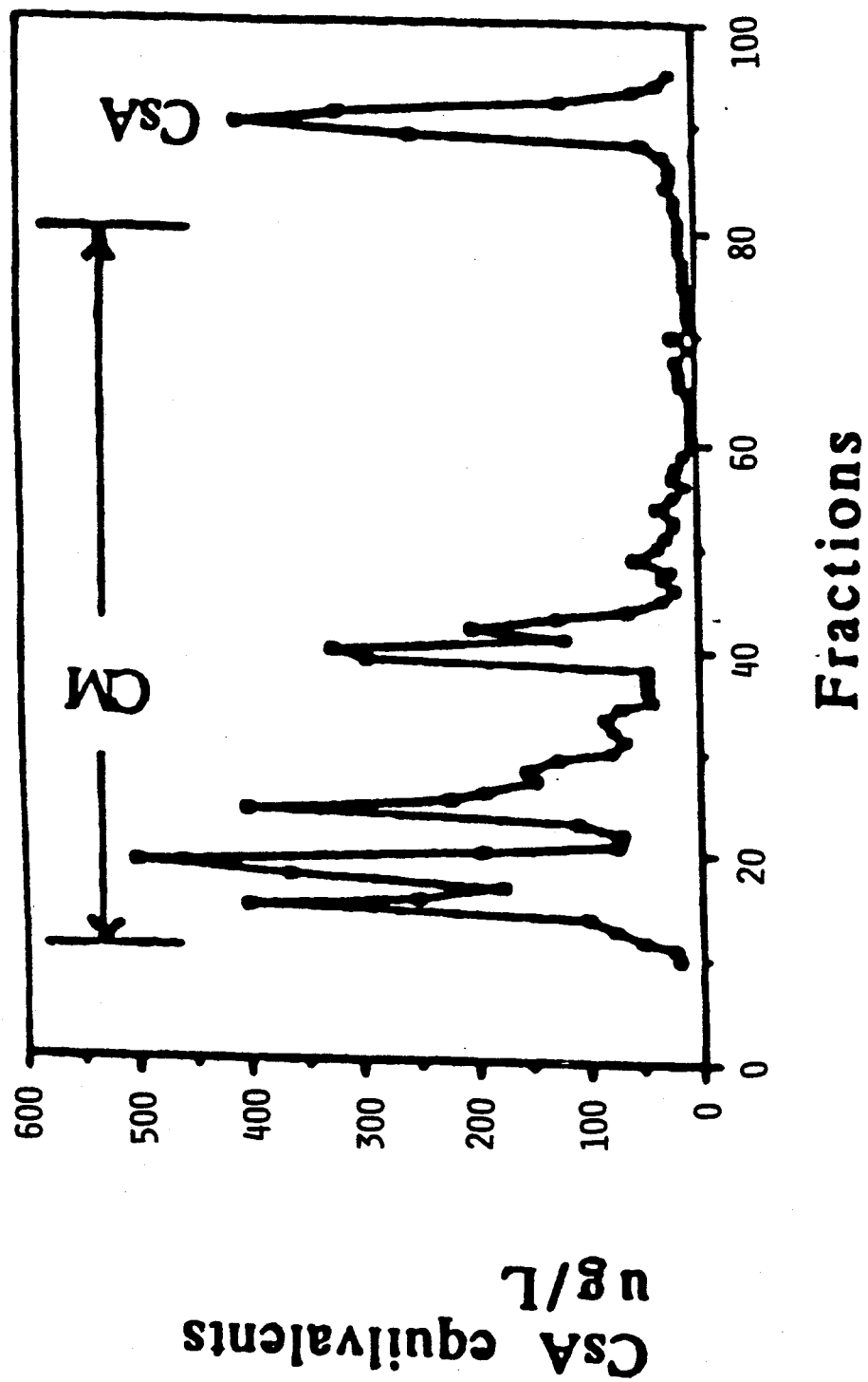
FIG. 3B shows the resulting chromatogram where C8 columns in tandem with isocratic elution are employed in the HPLC.
Figure 3C:
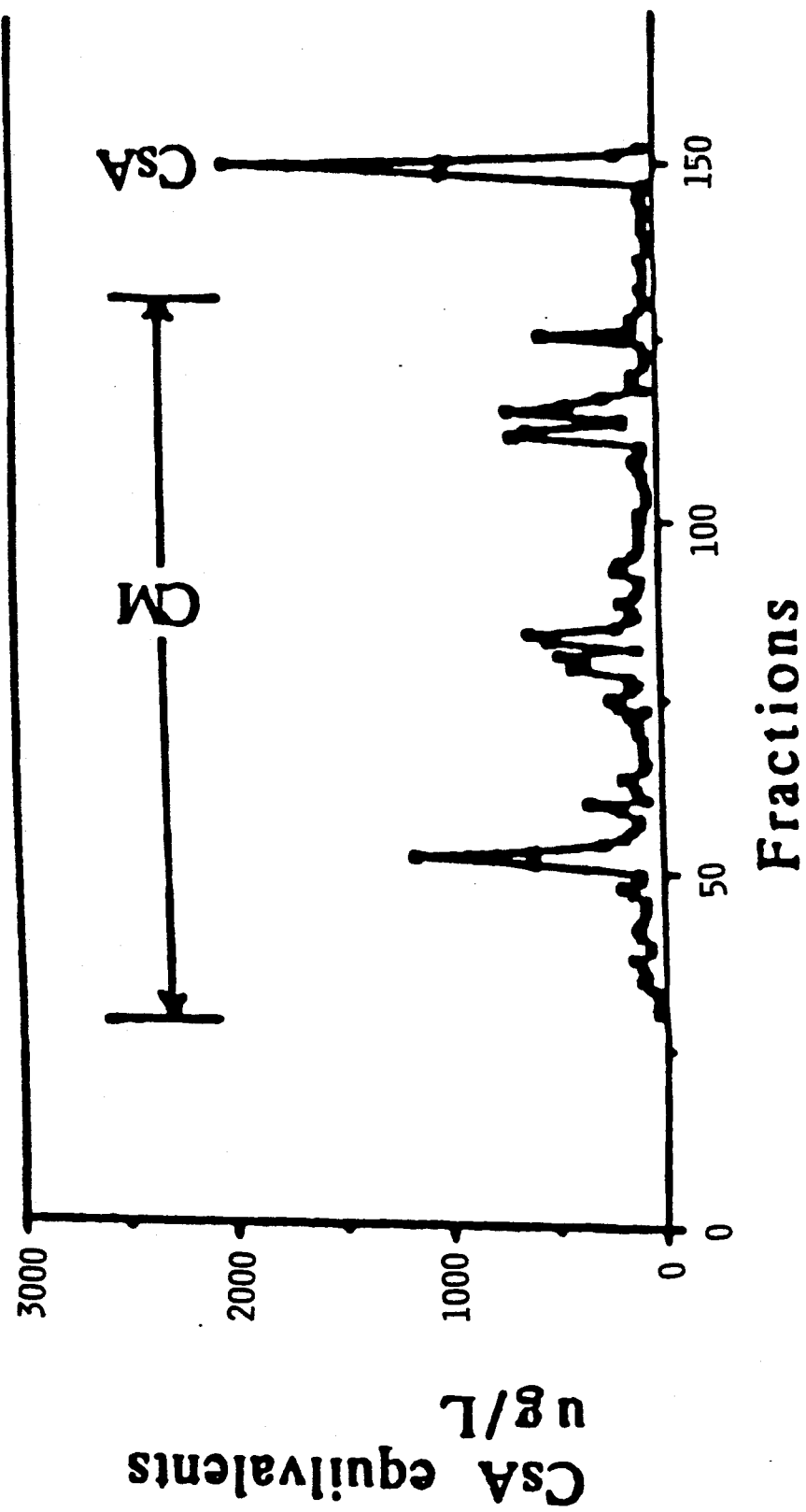
FIG. 3C shows the resulting chromatogram where C8 columns in tandem with linear gradient elution are employed in the HPLC.

Representative HPLC and polyclonal antibody RIA profiles of CM and CsA form urine samples are shown in FIG. 3. The same 24-hour urine sample from a CsA treated liver transplanted recipient was analyzed using the different HPLC methods. In all of the HPLC methods, CsA was separated from its metabolite fractions. CsA parent peak was identified with a CsA standard (Sandoz) displaying similar retention time off the HPLC. CM were separated and eluted off either C8 or C18 columns. The CM were eluted off with either an isocratic mobile phase (FIG. 3A and 3B) or a linear gradient of two mobile phases (FIG. 3C). When separated under identical isocratic conditions, using either a single C18 or C8 columns, CM eluted either as one large to four closely associated large peaks. FIG. 3A shows representatively CM eluted off a single C8 column.

Linking two C8 columns in tandem and eluting CM and CsA isocratically produced eight to nine CM peaks in addition to the parent peak (FIG. 3B). These peaks, however, are closely eluted adjacent to each other, making collection of individual peaks difficult.

In an effort to resolve the CM peaks to their baseline, linear gradient elution of the CM off tandem C8 columns was carried out (FIG. 3C). Gradient elution resolved many CM peaks to their baseline. In addition, four to five more CM peaks were separated producing a profile of at least 13 CM peaks in addition to the CsA parent.

FIG. 4 illustrates the use of gradient HPLC and polyclonal antibody RIA in the analysis of different biological fluids from a representative CsA treated liver transplant patient. The biological fluids investigated are the urine, bile and whole blood of the individual.

Figure 4A:
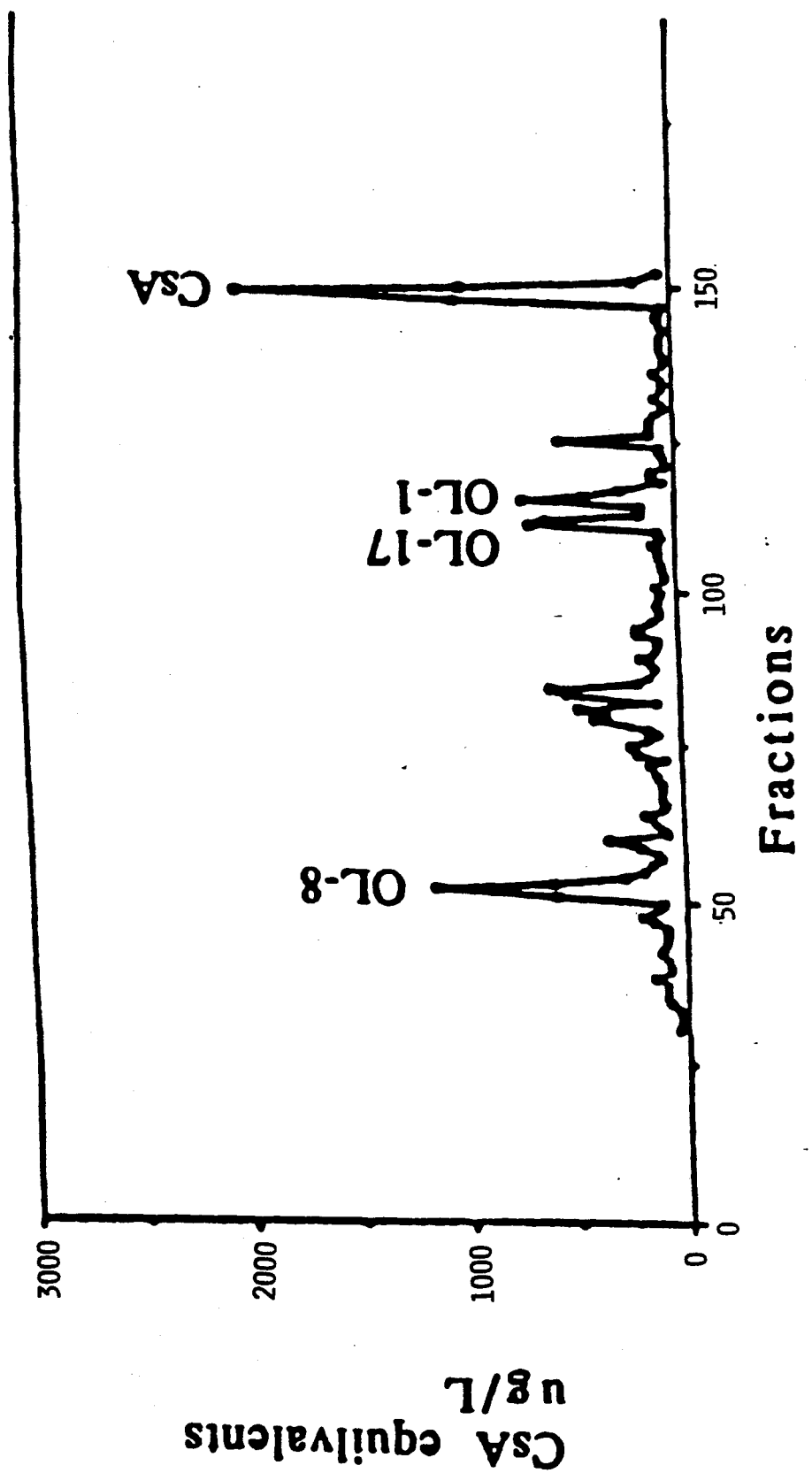
FIG. 4 shows gradient HPLC/polyclonal antibody RIA chromatograms from urine (A), bile (B) and whole blood (C) samples of a CsA treated liver transplant patient.
Figure 4B:
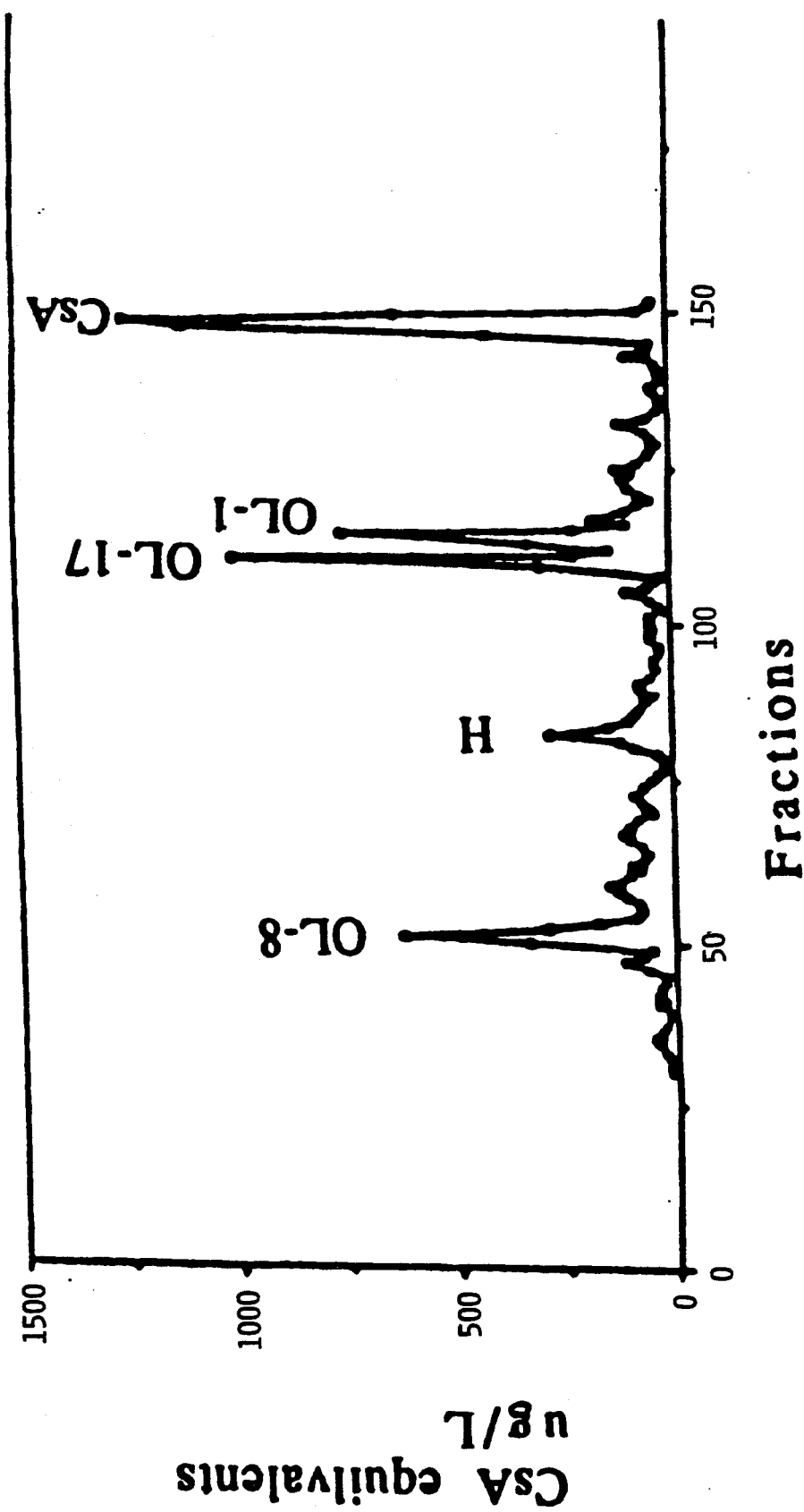
Figure 4C:
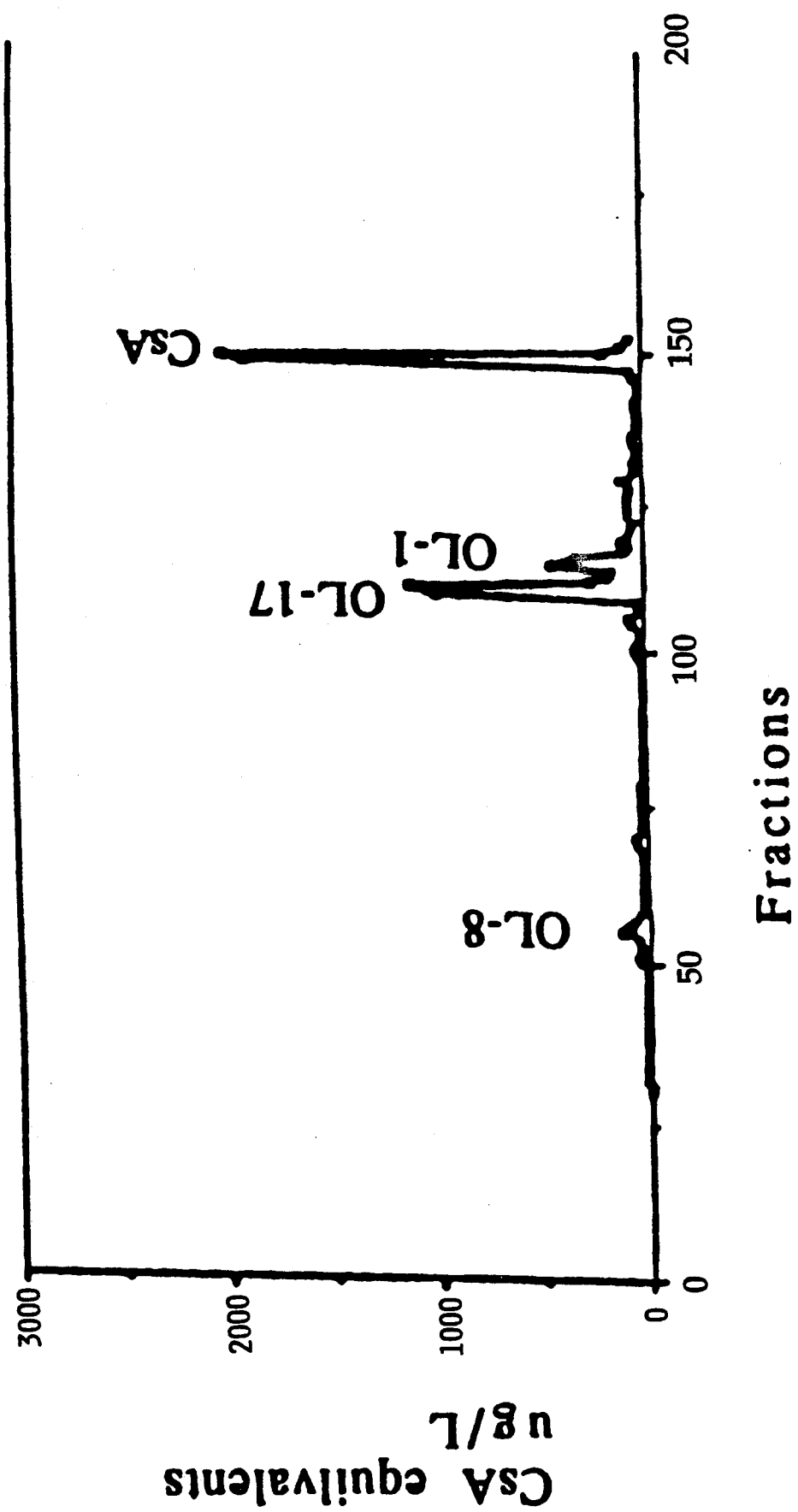

FIG. 4A shows a urinary CM and CsA profile. As shown in the figure, gradient HPLC is able to resolve a minimum of 13 CM from the urine sample. Among these 13 CM are eight equivalents. Included among these eight CM are the CM OL-8, OL-17 and OL-1. CM standards corresponding to CM OL-8, OL-17 and OL-1 coeluted with the respective CM peaks at similar retention times. The remaining peaks in FIG. 4A are polyclonal antibody recognized CM as yet to be identified.

Figure 5:
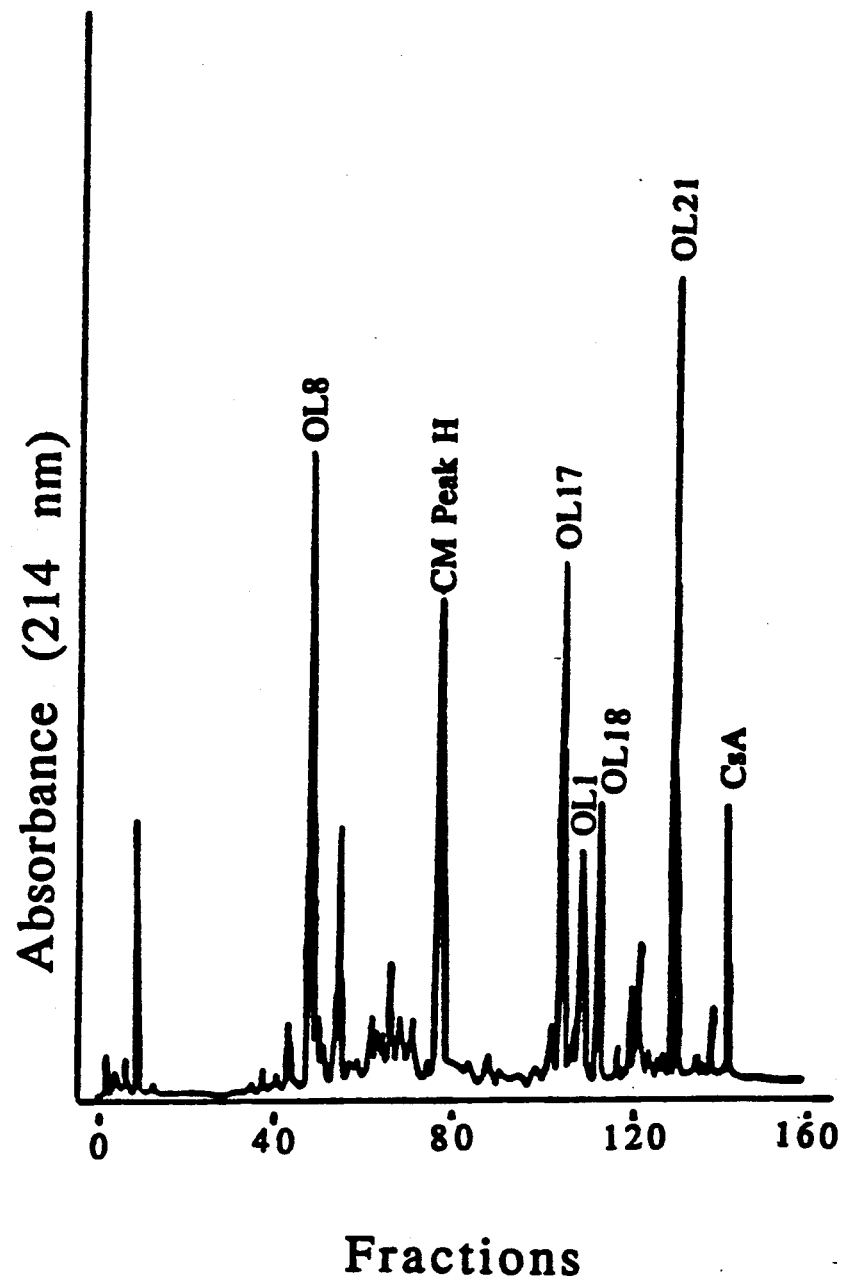
FIG. 5 shows a UV chromatogram of biliary derived CM and CsA from a CsA treated liver transplant recipient.

The biliary CM profile (FIG. 4B) indicates 14 CM peaks were recognized by the polyclonal antibody. Four of these peaks are major CM. Three of the CM peaks coeluted with the OL-8, OL-17 and OL-1 standards. A fourth unknown CM was given the designation of CM peak H. This CM peak demonstrated polarity off the gradient HPLC in between the very polar CM OL-8 and the less polar CM OL-17. It has a Rf value of 0.54 (Table 1). The striking feature of this CM is that although it displaced an amount slightly above 250 $\mu$g/L CsA equivalents in the RIA profile, it demonstrated a large absorbance in the U.V. profile (FIG. 5). A comparison of the UV and RIA detected CM profiles (FIG. 4 and FIG. 5) showed that the majority of the UV absorbing peaks are CM and CsA.

Studying the whole blood profile as detected by RIA (FIG. 4C), the predominating CM is shown to be OL-17. Other recognized CM are OL-1 and possibly OL-8. All whole blood profiles from liver as well as other different organ transplant individuals investigated were found to be similar. CsA parent in the whole blood samples were routinely quantitated using the monoclonal specific antibody in a RIA and were found to be within the therapeutic range of 150 to 300 ng/ml. The number of CM that one may recover from biological fluids of CsA treated individuals varies.

Figure 6A:
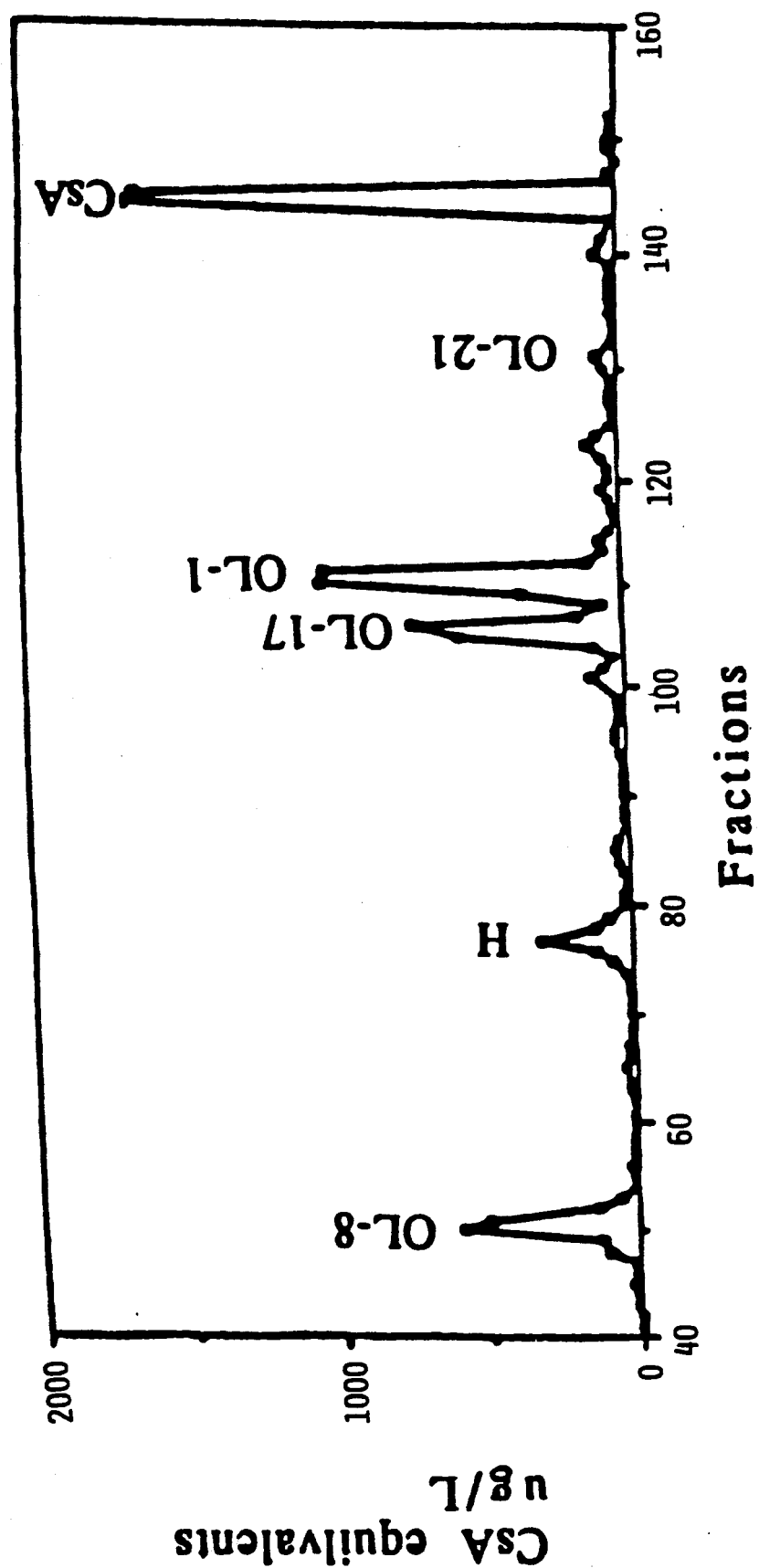
FIG. 6 is a gradient HPLC/RIA chromatogram of CM and CsA derived from a bile sample and as detected by polyclonal antibody (FIG. 6A), as detected by monoclonal nonspecific antibody (FIG. 6B), and as detected by monoclonal specific antibody (FIG. 6C).
Figure 6B:
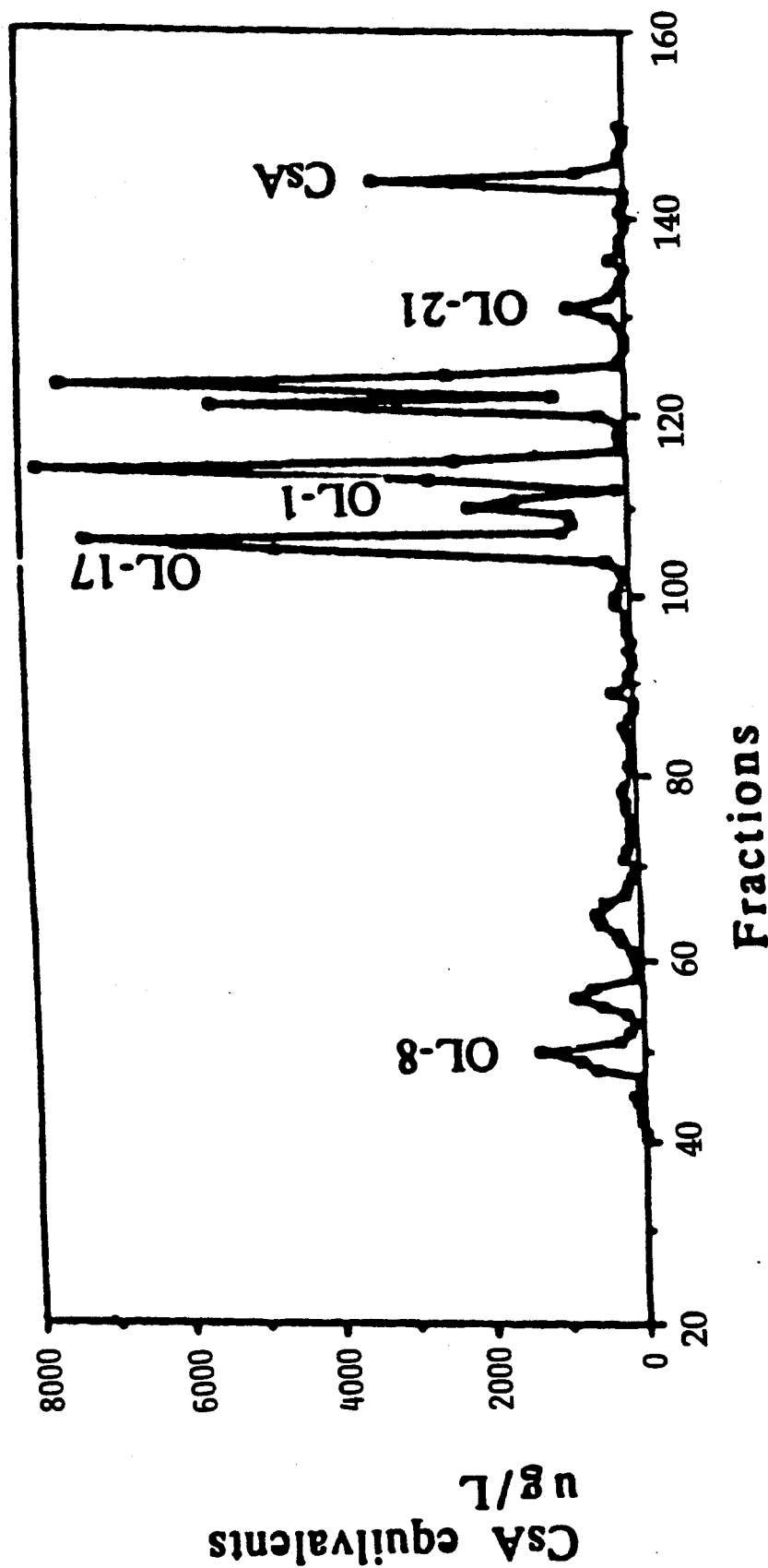
Figure 6C:
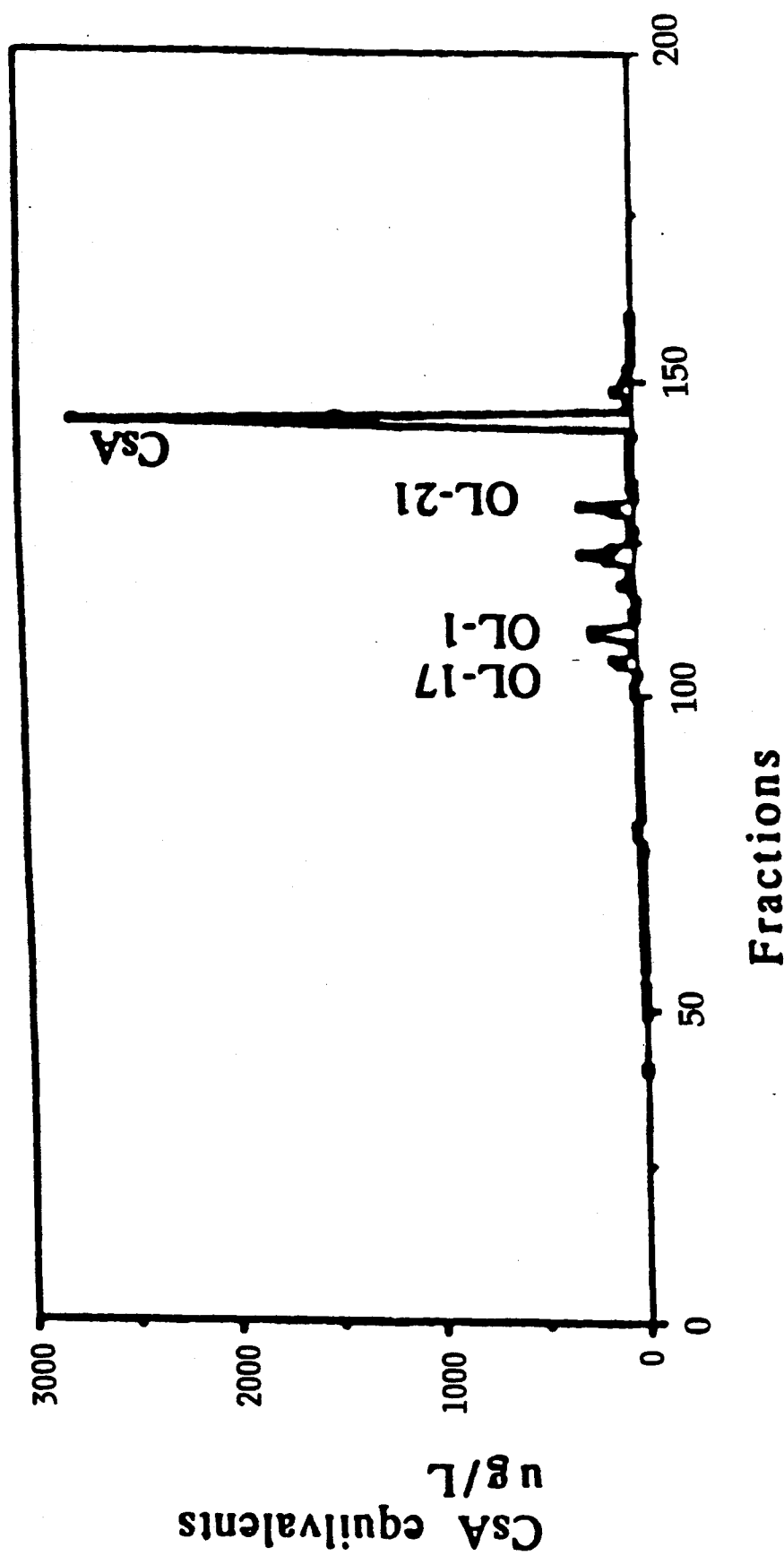

Shown in FIG. 6 are gradient HPLC/RIA profiles of bile derived CM and CsA from a CsA treated liver transplant patient as detected by three different anti-cyclosporin antibodies using a RIA. The CM peaks recognized by the three different antibodies are different. The polyclonal antibody profile (FIG. 6A) showed the broadest spectrum of CM peaks. It recognized a minimum of ten peaks that included the four major CM peaks shown in the bile derived CM and CsA chromatogram FIG. 4B. The CM ranged from the very polar OL-8 to the less polar OL-21. FIG. 6B shows the CM and CsA profiles as detected by monoclonal antibodies which are nonspecific to CsA. The nonspecific monoclonal antibody recognized a split spectrum of CM peaks. The very polar CM such as OL-8 and the less polar CM OL-17, OL-1 and OL-21 were very clearly recognized. However, the highest intermediate polar CM peak H was not detected. The third CM chromatogram (FIG. 6C) was produced using monoclonal antibodies specific to CsA parent. Generally, the antibodies recognized the CsA parent very well and did not recognize CM very well. In particular, the most polar CM such as OL-8 and intermediate polar CM like peak H were not recognized. However, there was some recognition of the less polar CM such as OL-1 and OL-21.

In Table 2, the amount of CM peaks recovered is expressed as a mean value percentage of the total cyclosporins present in the bile. For the five patients studied, the mean value % of CM and CsA are presented in decreasing amounts: OL-17 (16%)>OL-8 (11%)>CM peak H (9.2)>OL-21 (8.4%)>OL-1 (5%), OL-18 (5%)>CsA parent (4.5%). Ol-17 is the most abundant metabolite found in the bile. CsA parent is the least abundant of the cyclosporins in the bile.

In an attempt to further quantitate the CM that may be recovered from the bile, 100 ml of bile was extracted as described in Example 1(a) above. CM peaks were fractionated and isolated through semi-preparative gradient HPLC. The fractionated CM were then dried and reconstituted in 1 ml of isocratic mobile phase. A 250 μL aliquot of the rehydrated CM was then quantitated with known amounts of CsA internal standard using an analytical gradient HPLC. The results were expressed as amount of material per liter of bile. A range of 300 μg/L for OL-18 to 853 μg/L for OL-17 is observed and is shown in Table 2.

EXAMPLE 3

To further characterize the CM, resolved CM were subjected to fast atomic bombardment mass spectroscopy (FABMS) and nuclear magnetic resonance (NMR). CsA and CM were extracted from bile and separated on a preparative gradient HPLC as described above in Examples 1 and 2 and then subjected to FABMS or NMR. Mass i) FABMS FABMS was performed using conventional techniques. CsA and CM were introduced in the FAB source either as a dispersion in a mixture of glycerol with a trace of glacial acetic acid, or as a solution in methanol. All spectra were recorded on a Finnigan MAT 312 double focussing reversed geometry mass spectrometer, mounted with a saddle field atom gun (Ion Tech) and coupled to a super INCOS data system. High-purity research grade Xenon (99.95%) was used as the bombardment gas (8 kV), and the resulting positive ions were extracted (3 kV) into the mass analyzer. A mass range between 500 and 1,000 daltons was scanned exponentially in ten seconds. A nominal resolution of 1,000 daltons was maintained, and the electron multiplier was kept at a value of 2.4 kV.

Resolved CM peaks having retention times identical to OL-17, OL-1, OL-8, CM peak H and CsA parent were subjected to FABMS. CsA and the four CM are presented in FIGS. 7-11. FIG. 7 shows the partial positive ion FAB mass spectra of CsA parent with a molecular ion at 1203 mass units. The CM, OL-17 displayed a molecular ion at 1219 mass units (FIG. 8). The CM, OL-1 also showed a molecular ion at 1219 mass units (FIG. 9). Comparing the CM molecular mass of OL-17 and OL-1 to that of the parent strongly supports the addition of a hydroxyl group, or 16 mass units to the CsA structure with the removal of a proton. The molecular mass of OL-8 was 1235 mass units (FIG. 10). This suggests that the metabolic addition of two hydroxyl groups minus two protons to CsA has taken place. CM peak H revealed a molecular mass ion at 1205 mass units (FIG. 11).

Comparing the molecular ions of CsA and CM peak H, it is logical to postulate that adding two protons to the cyclosporin structure yields dihydro-cyclosporin A with a molecular mass of 1205. This, however, does not accord with the elution of the cyclosporin analogue dihydro-CsA, through the gradient HPLC. Dihydro-CsA eluted off the gradient HPLC in very close proximity to the CsA parent, whereas CM peak H eluted much earlier than the CsA parent as shown in FIG. 5. Thus CM peak H cannot be dihydro-cyclosporin A.

Detailed FABMS analysis (MIKES-mass ion kinetic energy) of CM peak H was performed using approximately 20 μg of resolved CM peak H. The results set out in Table 3 show that there is stability in the fragment ions between the amino acids 1 to 8 in the CsA molecule. Fragment ions between amino acids 9 and 10 were highly variable suggesting modifications of CsA occurred at these positions. In particular, based on FABMS, there is 95% confidence that hydroxylation is in AS9 and demethylation is AA10.

CM peak H possesses similar retention time off the gradient HPLC as the rabbit bile derived carboxylic acid CM 203-14 208 (Mauer, G. et al, Transplant. Proc. 18:25, 1985). The Rf value of CM peak H is 0.54 and the Rf value of CM 203-208 is 0.56. However, mass spectroscopy was able to show that the two CM were different as their masses were different. CM 203-208 possess a molecular mass of 1233 as opposed to CM peak H which has a molecular mass of 1205. Thus CM 203-208 is not the same as CM peak H.

ii) NMR

Proton NMR spectra of CsA parent and CM peak H were analyzed at 300 mHz in $CDCl_2$ using tetrasilane as the internal standard.

Figure 12B:
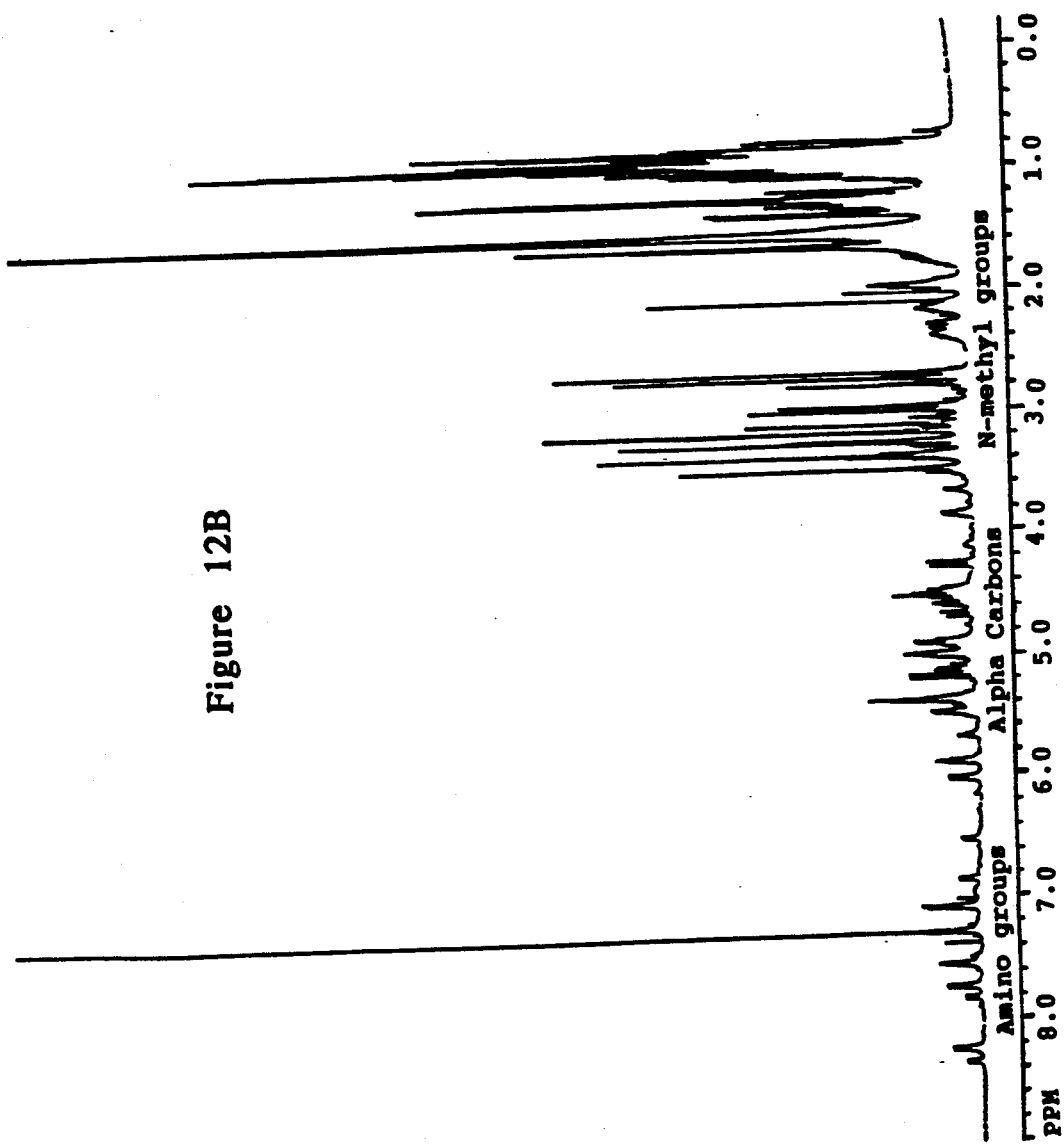

Proton NMR profiles of both the CsA parent and the CM peak H are shown in FIG. 12A and 12B respectively. Comparing the two NMR spectrum at the N-methyl group resonances section (2.6 to 3.6 PPM), one can observe that there is a decrease in N-methyl group peak heights in the metabolite when compared to peak heights for the CsA parent. This data supports an N-demethylated structure for CM peak H. In addition, the spectrum also showed that there was twice as many resonance lines in the spectrum of CM peak H as in the CsA parent. The doubling of spectral lines in the CM spectrum suggests that there are two closely related CMs within peak H. These two CM could be isomers of each other.

EXAMPLE 4

Effects of CsA and CM on DNA, RNA and Protein Synthesis

CM were isolated from bile using a procedure similar to that described in Example 1. Briefly, one part bile was extracted with one part diethyl ether, USP grade (Fisher Scientific Co., Toronto, Canada) three times. The ether extracts were combined and evaporated under vacuum to dryness at 45° C. The residue was reconstituted in acetonitrile:methanol:water (50:20:30). Reconstituted CM were separated by a Waters gradient HPLC system (Waters Associates, Milford, Mass.). The reconstituted residue was chromatographed on a 15-cm μBondapak/C18 column (Waters Associates, Milford, Mass.) and the CM and CsA were collected on the first and second 10 ml, respectively. To detect the resolved CM and parent CsA, 150 μl of each eluate were assayed by standard radioimmunoassay using specific and non-specific monoclonal antibodies against parent CsA, and by UV spectroscopy to determine the relative preparation of individual metabolites (Cheung, F. et al, Transplant. Proc. 20:602, 1988; Abecassis, M. et al, Can. J. Surg. 31:145, 1988).

The elution profile of the total CM from the bile of the orthotopic liver transplant recipients demonstrates that the major constituents of the extracted CM were OL-17, OL-1, OL-8, and the polar peaks H and C (FIG. 13). The area under the curve was calculated by an internal standard quantification method using Waters 740 Data AUC module (Waters Millipare, Milford, Mass.). The AUC for total CM was 245 nm, and the relative areas of major CM as a percentage of the total CM were OL-17=25.5%, peak C=15.31%, peak H=6.33%, OL-1=5.1%, and OL-18=4.1%, which was 56.3% of the total CM as determined by UV spectroscopy (Table 4). The parent CsA was not present in CM by both HPCL/RIA.

Renal glomerular mesangial cells, derived from collagenase treated glomeruli from Sprague-Dawley rates, were cultured in Dulbecco's modified Eagle's medium (Gibco Laboratories, New York, N.Y.) supplemented with 20% fetal calf serum and insulin. LLC-PK$_1$ cells, ad established pig renal epithelial cell line were cultured in DME fortified with 10% fetal calf serum. L2 cells, an established murine lung cell line, were propagated in ADME fortified with 10% fetal calf serum, 25μg/ml chlortetracycline hydrochloride grade II and buffered with 15 mM HEPES and 4 mM glutamine.

To assess the effects on DNA and RNA synthesis, $2 \times 10^4$ cells were incubated in either the test solution or appropriate control of Cremaphor or ethanol (metabolites). The cells in the presence of the test solutions were incubated for 19 hours, following which 1 μCi$^3$H thymidine (DNA synthesis) (New England Nuclear, sp. act. 20 Ci/mmol) and $^3$H uridine (RNA synthesis) (New England Nuclear, sp. act 22 Ci/mmol) were added, and the cells cultured for 5 hours longer, and then harvested and counted.

For protein synthesis $1 \times 10^5$ cells were added to each test solution, incubated for 19 hours, and then 2.5 μCi of CL-4,5$^3$H leucine (Schwarz/Mann. sp. act. 59 Ci/mmol) was added and the cells incubated for a further 5 hours. Then 0.05% trypsin/0.5 mM EDTA in phosphate-buffered saline was added to an equal volume of 0.1% bovine serum albumin and an equal volume of 20% trichloroacetic acid. The cells were incubated in this solution for 30 min and then harvested and counted. Percent inhibition was calculated as follows:

$$\% \text{ inhibition} = 1 - \frac{(cpm_A - cpm_B)}{cpm_A} \times 100$$

where $cpm_A$=counts per minute of cells cultured in Cremaphor EL or ethanol, $cpm_B$=counts per minute of cells cultured with CsA or CM.

FIG. 14 shows the effects on DNA (A), RNA (B), and protein (C) synthesis of the renal epithelial (■), renal mesangial (▨) cell lines, and murine lung cell line L2 (▣).

FIG. 15 shows the effects of the individual metabolites OL-1, OL-17, OL-18, C(OL-8) and H on (A) DNA, (B) RNA and (C) protein synthesis in renal mesangial cells.

Figure 14B:
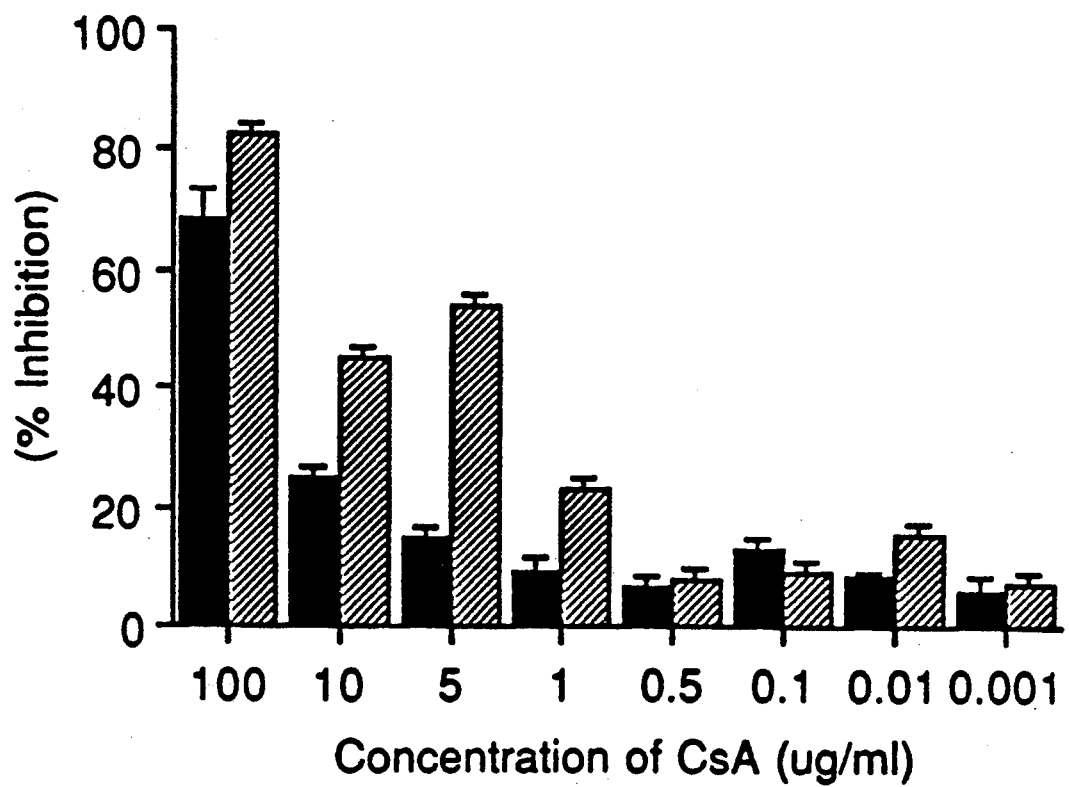
Figure 14C:
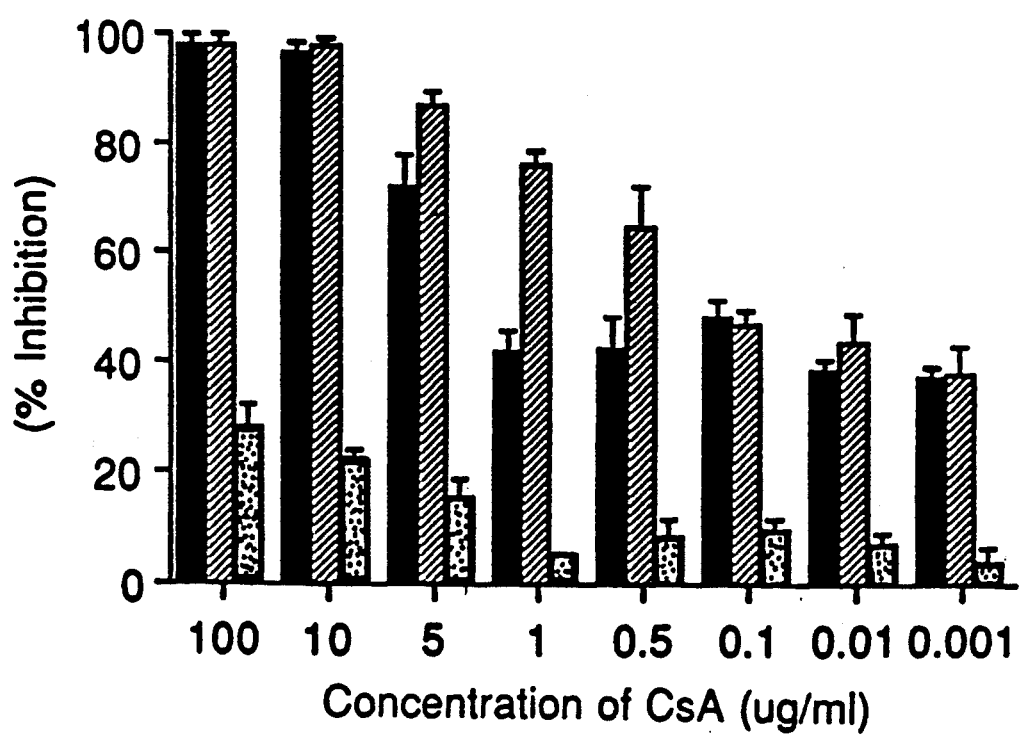
Figure 15B:
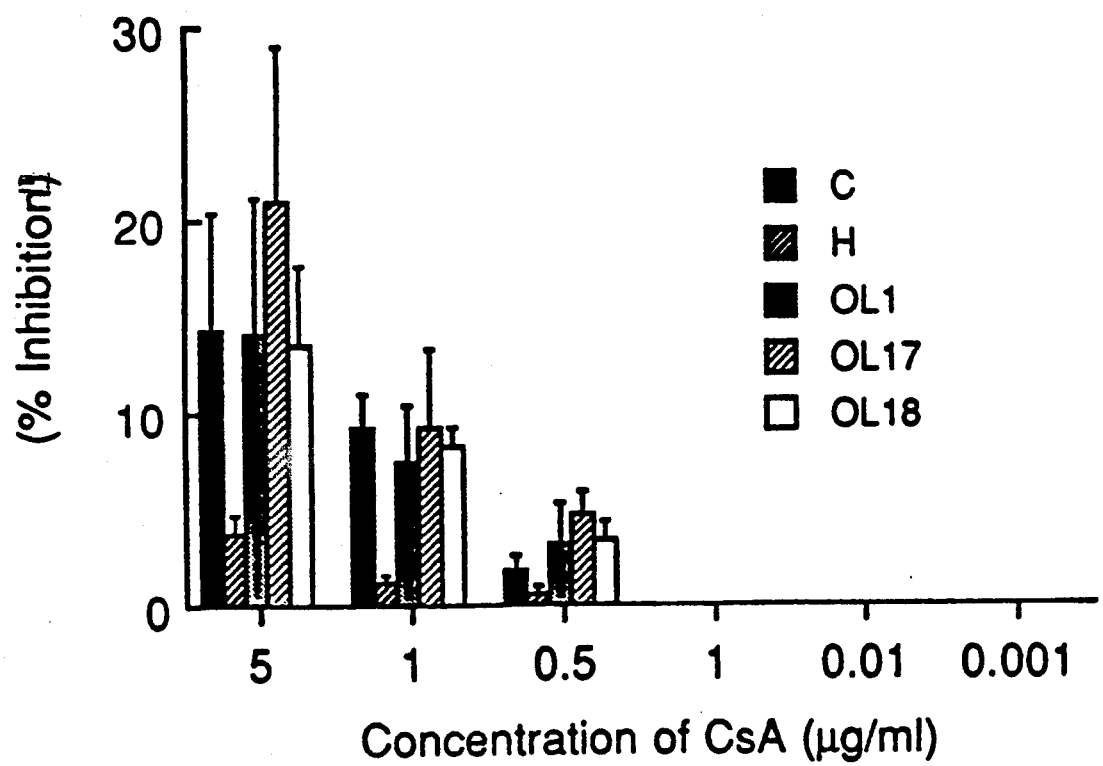
Figure 15C:
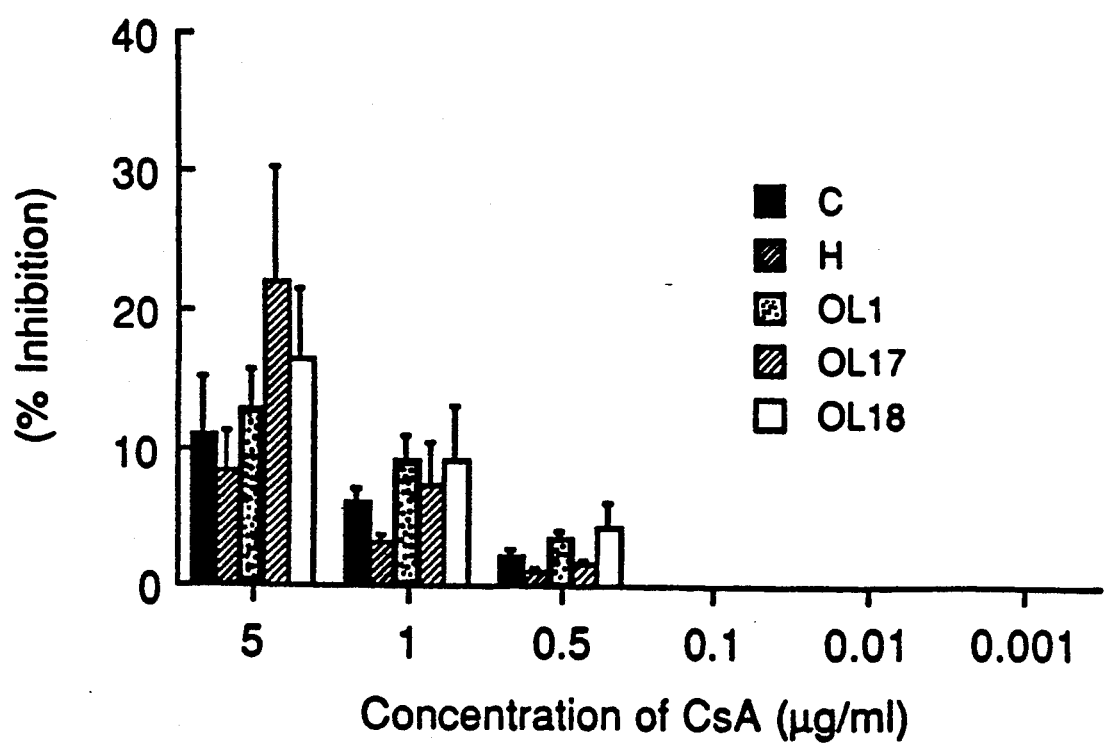

Significant dose-dependent inhibition of DNA synthesis was observed in both the renal epithelial and mesangial cell lines. Inhibition of DNA synthesis in the control, L2 cell line was observed only at concentrations of 5 μg/ml or greater (FIG. 14A). CsA inhibited RNA synthesis in does-related fashion in both renal cell lines (FIG. 14B). Similarly, significant dose-related inhibition of protein synthesis was observed in both renal cell lines to 1 ng/ml (FIG. 14C). In contrast to CsA, metabolites C(OL-8), H, OL-1, OL-17, and OL-18 had no inhibitory effects on DNA, RNA, and protein synthesis of the renal epithelial and murine lung cell-lines, whereas individual CM had some inhibitory effects on DNA, RNA, and protein synthesis of the renal messengial cells only at concentrations greater than 1 and 5 μg/ml, far in excess of the recommended therapeutic range (FIG. 15A, 15B and 15C). Metabolite H appeared to demonstrate the least inhibitory effects on DNA, RNA and protein synthesis of the renal messengial cells as compared to metabolites C(OL-8), OL-1, OL-17, and OL-18.

EXAMPLE 5

Effects of CsA and CM Peak H on Phospholipase A$_2$ Activity

CsA was found to inhibit phospholipase A$_2$ activity greater than 50% at concentrations of 1 mg/ml or greater, whereas CM Peak H had no such inhibitory activity. As phospholipase A$_2$ is a direct measure of mesangial prostaglandin biosynthesis, this suggests that CM peak H does not interfere with formation of prostaglandins which is known to be associated with an causative of cyclosporin induced nephrotoxicity.

EXAMPLE 6

Effect of CM Peak H on IL1, IL2, and IL2 Receptor Activity

The effect of CM Peak H on IL1, IL2 and IL2 receptor activity was studied using the method as described in Freed, B. M., Transplantation 43:123, 1987. CM Peak H was found to be as effective as cyclosporine A in inhibiting formation of, and action of IL1, IL2 and IL2 receptors.

TABLE 1

Rf values for cyclosporine metabolites and parent. CsA parent is assigned a Rf value of 1.000 and cyclosporine metabolites Rf values are assigned in relation to its value.

| Cyclosporines | Rf Value Assigned |
|---|---|
| CsA | 1.000 |
| OL-8 | 0.346 |
| CM Peak H | 0.546 |
| 203-208 | 0.569 |
| OL-17 | 0.735 |
| OL-1 | 0.769 |
| OL-18 | 0.793 |
| OL-21 | 0.906 |

TABLE 2

Statistical results for CsA parent/metabolite data from bile collected from five CsA treated liver transplant individuals.

| Normenclature of the cyclosporine molecule. | Mean % of total concentration of cyclosporine (mean value, n = 5) | Amount of cyclosporine per liter of bile as determined with internal standard. |
|---|---|---|
| OL-8 | 10.86 ± 2.4 | 640 ug/L |
| CM peak H | 9.20 ± 2.9 | 536 ug/L |
| OL-17 | 16.00 ± 4.4 | 853 ug/L |
| OL-1 | 5.23 ± 2.0 | 364 ug/L |
| OL-18 | 5.11 ± 0.7 | 300 ug/L |
| OL-21 | 8.4 ± 2.6 | 510 ug/L |
| CsA Parent | 4.50 ± 0.96 | — |

TABLE 3

Results of Detailed FABMS Analysis of Peak H

~20 ug of H was analyzed by FABMS. The mass of all fragments was studied. There are 11 amino acids present in a CsA molecule. The following analysis was carried out assuming that CsA is a linear molecule.

| AA: | 1 | 2 | 3 | 4 | 5 | 6 | 7 | 8 | 9 | 10 | 11 |
|---|---|---|---|---|---|---|---|---|---|---|---|
| MW: | 183 | 85 | 71 | 127 | 99 | 127 | 71 | 71 | 127 | 127 | 113 |

Fragments:

MW: AA 1-2: 268  AA 1-3: 339  AA 1-4: 466
AA 1-5: 565  AA 1-6: 692  AA 1-7: 763
AA 1-8: 834

TABLE 3-continued
Results of Detailed FABMS Analysis of CM Peak H

1. Fragment with MW of 183 is present. AA 1 is intact.
2. Fragment with MW of 85 is present. AA2 is intact.
3. Fragment with MW of 99 is present. AA 5 is intact.
4. Fragment with MW of 113 is present. AA 11 is intact.
5. Fragments with MWs of 127 and 71 are present. However, there are 4 AAs with MW of 127 and 3 AAs with MW of 71.
6. Fragment with MW of 268 is present. AA 1-2 is intact.
7. Fragment with MW of 339 is present. AA 1-3 is intact.
8. Fragment with MW of 466 is present. AA 1-4 is intact.
9. Fragment with MW of 565 is present. AA 1-5 is intact.
10. Fragment with MW of 693 is present. AA 1-6 (MW of 692) is probably intact.
11. Fragment with MW of 763 is present. AA 1-7 is intact.
12. Fragment with MW of 834 is present. AA 1-8 is intact.
13. Based on the above results, it appears that the metabolism of hydroxylation and demethylation (+OH, −CH3) are in either AA 9 or AA 10.
14. If hydroxylation (+OH) occurs in AA 9, a fragment [AA 1-8-AA9 (+OH)] of MW of 961 + 17 − 1 = 977 will be present. Fragments with MW of 975 were present. Hydroxylation may be in AA 9.
15. If hydroxylation (+OH) occurs in AA9 and demethylation occurs in AA10 [AA 1-8-AA9(+OH)-AA10(−CH3)], this fragment with a MW of 1090 (1088 + 17 − 1 − 15 + 1 = 1090) will be present. Fragments with MW of 1088 were present. It indicates that hydroxylation is in AA9 and demethylation is in AA 10.

Other fragments:

16. Fragment AA11-10(demethylation): MW = 113 + 127 − 15 + 1 = 226. From FABMS, fragments with MW of 226 were present.
17. Fragment AA1-11-10(demethylation): MW = 226 + 183 = 409. From FABMS, fragments with MW of 410 were present.
18. Fragment AA2-1-11-10(demethylation): MW = 409 + 85 = 494. From FABMS, fragments with MW of 495 were present.

TABLE 4
Relative Percentage Composition of the Total CM

| Compounds | AUC (mm) | Percentage of total CM |
|---|---|---|
| OL-17 | 62.5 | 25.5 |
| C | 37.5 | 15.3 |
| H | 15.5 | 6.3 |
| OL-1 | 12.5 | 5.1 |
| OL-18 | 10.1 | 4.1 |
| Other fractions | 107.0 | 43.7 |
| Total | 245.0 | 100% |

*The major fractions of the extracted total CM are listed in the order of decreasing relative proportions. The major CM were OL17, OL1, OL18, and peaks C and H, which were 56.3% of the extracted total CM.

We claim:

1. A cyclosporine metabolite having a molecular weight determined by mass spectrometry of about 1205 and having the following properties:
   a) being immunologically distinct from cyclosporine metabolites OL-1, OL-17 and OL-8;
   b) being more polar than OL-1 or OL-17 and less polar than OL-8 when eluated from a gradient high performance liquid chromatography;
   c) being extractable from bile of test animals which have been administered cyclosporine A; and
   d) being substantially free of other cyclosporine metabolites and cyclosporine A, or a physiologically acceptable salt or stereoisomer thereof.

2. A cyclosporine metabolite substantially having the structure of cyclosporine A and having a hydroxylated αN-methylated α-leucine at the 9-position and an α-N-demethylated α-leucine at the 10-position, and wherein the cyclosporine metabolite is substantially free of other cyclosporine metabolites and cyclosporine A, or a physiologically acceptable salt or stereoisomer thereof.

3. A cyclosporine metabolite of the formula:

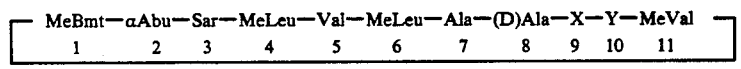

wherein X is hydroxylated α-N-methylated leucine, and Y is α-N-demethylated leucine, and wherein the cyclosporine metabolite is substantially free of other cyclosporine metabolites and cyclosporine A, or a physiologically acceptable salt or stereoisomer thereof.

4. A substantially purified cyclosporine metabolite of the formula II

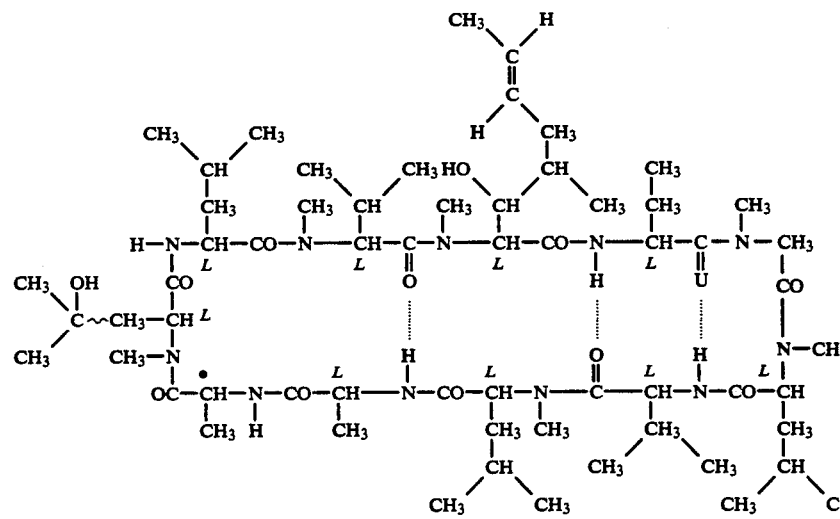

and a physiologically acceptable salt or stereoisomer thereof.

5. A pharmaceutical composition comprising a cyclosporine metabolite as claimed in claim 2 and a pharmaceutically acceptable diluent or carrier.

6. A pharmaceutical composition comprising a cyclosporine metabolite as claimed in claim 3, and a pharmaceutically acceptable diluent or carrier.

7. A pharmaceutical composition comprising a cyclosporine metabolite as claimed in claim 4 and a pharmaceutically acceptable diluent or carrier.

8. A pharmaceutical composition as claimed in claim 6 or 7 for use in the prophylaxis and treatment of diseases and conditions requiring a reduction of the immune response.

9. A method of inducing immunosuppression in a patient comprising administering to said patient an effective amount of a cyclosporine metabolite as claimed in claim 3 or 4.

10. A method of preventing and treating conditions requiring a reduction of the immune response in a patient which comprises administering to said patient an effective amount of cyclosporine metabolite as claimed in claim 1, 2 or 3.

* * * * *